United States Patent
Tamang et al.

(10) Patent No.: US 9,403,779 B2
(45) Date of Patent: Aug. 2, 2016

(54) COMBINATIONS OF HISTONE DEACETYLASE INHIBITORS AND EITHER HER2 INHIBITORS OR PI3K INHIBITORS

(71) Applicant: ACETYLON PHARMACEUTICALS, INC., Boston, MA (US)

(72) Inventors: David Lee Tamang, Watertown, MA (US); Min Yang, Newton, MA (US); Simon S. Jones, Boston, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 14/506,889

(22) Filed: Oct. 6, 2014

(65) Prior Publication Data

US 2015/0099744 A1    Apr. 9, 2015

Related U.S. Application Data

(60) Provisional application No. 61/888,207, filed on Oct. 8, 2013.

(51) Int. Cl.
| | | |
|---|---|---|
| *A61K 31/505* | (2006.01) | |
| *C07D 239/42* | (2006.01) | |
| *A61K 31/517* | (2006.01) | |
| *A61K 31/5377* | (2006.01) | |

(52) U.S. Cl.
CPC ............ *C07D 239/42* (2013.01); *A61K 31/505* (2013.01); *A61K 31/517* (2013.01); *A61K 31/5377* (2013.01)

(58) Field of Classification Search
CPC .. C07D 405/04; C07D 239/42; A61K 31/517; A61K 31/505
See application file for complete search history.

(56) References Cited

U.S. PATENT DOCUMENTS

| | | | |
|---|---|---|---|
| 3,549,633 A | 12/1970 | Grabowski et al. | |
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,994,362 B2 | 8/2011 | Schreiber et al. | |
| 8,148,526 B1 * | 4/2012 | van Duzer | C07C 259/06 544/332 |
| 8,394,810 B2 | 3/2013 | van Duzer et al. | |
| 8,609,678 B2 | 12/2013 | van Duzer et al. | |
| 8,614,223 B2 * | 12/2013 | van Duzer | C07D 239/42 514/275 |
| 9,145,412 B2 | 9/2015 | van Duzer et al. | |
| 2004/0266769 A1 | 12/2004 | Bressi et al. | |
| 2005/0119305 A1 | 6/2005 | Naka et al. | |
| 2006/0239909 A1 | 10/2006 | Anderson et al. | |
| 2007/0093413 A1 | 4/2007 | Schreiber et al. | |
| 2007/0149495 A1 | 6/2007 | Bressi et al. | |
| 2008/0182865 A1 | 7/2008 | Witta et al. | |
| 2008/0207590 A1 | 8/2008 | Deziel et al. | |
| 2009/0023786 A1 | 1/2009 | Miller et al. | |
| 2009/0209590 A1 | 8/2009 | Mazitschek et al. | |
| 2009/0305384 A1 | 12/2009 | Grozinger et al. | |
| 2009/0312363 A1 | 12/2009 | Bradner et al. | |
| 2010/0137196 A1 | 6/2010 | Schreiber et al. | |
| 2010/0152254 A1 | 6/2010 | Bialer et al. | |
| 2010/0168463 A1 | 7/2010 | Hirata et al. | |
| 2010/0330197 A1 | 12/2010 | Higashiguchi et al. | |
| 2011/0218154 A1 | 9/2011 | Schreiber et al. | |
| 2013/0225543 A1 * | 8/2013 | Jones | A61K 31/165 514/171 |
| 2014/0011767 A1 | 1/2014 | Yang et al. | |
| 2014/0142104 A1 | 5/2014 | van Duzer et al. | |
| 2014/0142117 A1 | 5/2014 | van Duzer et al. | |
| 2014/0243345 A1 | 8/2014 | van Duzer et al. | |
| 2014/0249148 A1 | 9/2014 | van Duzer et al. | |
| 2014/0357512 A1 | 12/2014 | Jones et al. | |
| 2015/0045380 A1 | 2/2015 | van Duzer et al. | |
| 2015/0099744 A1 * | 4/2015 | Tamang | C07D 239/42 514/234.2 |
| 2015/0105358 A1 * | 4/2015 | Quayle | A61K 31/505 514/171 |
| 2015/0105383 A1 * | 4/2015 | Quayle | C07D 239/42 514/234.2 |
| 2015/0105384 A1 * | 4/2015 | Jones | C07D 417/12 514/235.2 |
| 2015/0105409 A1 * | 4/2015 | Quayle | C07D 239/42 514/262.1 |
| 2015/0150871 A1 * | 6/2015 | Quayle | A61K 31/4439 424/278.1 |
| 2015/0176076 A1 * | 6/2015 | Yang | A61K 31/505 514/275 |
| 2016/0030458 A1 * | 2/2016 | Jones | A61K 31/706 514/43 |

FOREIGN PATENT DOCUMENTS

| | | |
|---|---|---|
| EP | 2 524 918 A1 | 11/2012 |
| WO | 01/70675 A2 | 9/2001 |
| WO | 02/074298 A1 | 9/2002 |
| WO | 03/037869 A1 | 5/2003 |

(Continued)

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*

(Continued)

*Primary Examiner* — Alexander R Pagano
(74) *Attorney, Agent, or Firm* — Lathrop & Gage LLP; Brian C. Trinque

(57) ABSTRACT

The invention relates to combinations comprising an HDAC inhibitor and a Her2 inhibitor for the treatment of breast cancer in a subject in need thereof. The invention also relates to combinations comprising an HDAC inhibitor and a PI3K inhibitor for the treatment of breast cancer in a subject in need thereof. Also provided herein are methods for treating breast cancer in a subject in need thereof comprising administering to the subject an effective amount of one of the above combinations. Further provided are methods for inhibiting migration and/or invasion of a breast cancer cell in a subject by administering to the subject a HDAC6 specific inhibitor.

4 Claims, 5 Drawing Sheets

(56) References Cited

FOREIGN PATENT DOCUMENTS

| | | |
|---|---|---|
| WO | 03/076401 A1 | 9/2003 |
| WO | 03/076430 A1 | 9/2003 |
| WO | 2004/052869 A1 | 6/2004 |
| WO | 2005/012261 A1 | 2/2005 |
| WO | 2005/028447 A1 | 3/2005 |
| WO | 2005/030705 A1 | 4/2005 |
| WO | 2006/102557 A2 | 9/2006 |
| WO | 2006/123121 A1 | 11/2006 |
| WO | 2007/022638 A1 | 3/2007 |
| WO | 2007/091703 A2 | 8/2007 |
| WO | 2007/130429 A2 | 11/2007 |
| WO | 2007/144341 A1 | 12/2007 |
| WO | 2008/003801 A1 | 1/2008 |
| WO | 2008/033746 A2 | 3/2008 |
| WO | 2008/055068 A2 | 5/2008 |
| WO | 2008076447 A2 | 6/2008 |
| WO | 2008/091349 A1 | 7/2008 |
| WO | 2009/137462 A1 | 11/2009 |
| WO | 2009/137503 A1 | 11/2009 |
| WO | 2010/009155 A2 | 1/2010 |
| WO | 2010/011296 A2 | 1/2010 |
| WO | 2010/080996 A1 | 7/2010 |
| WO | 2010/131922 A2 | 11/2010 |
| WO | 2011/011186 A1 | 1/2011 |
| WO | 2011/019393 A2 | 2/2011 |
| WO | 2011/084991 A2 | 7/2011 |
| WO | 2011091213 A2 | 7/2011 |
| WO | 2011/146855 A1 | 11/2011 |
| WO | 2012068109 A2 | 5/2012 |
| WO | 2013/013113 A2 | 1/2013 |
| WO | WO 2013013113 A2 * | 1/2013 ............ C07C 259/06 |

OTHER PUBLICATIONS

L. Liu et al., 69 Cancer Research, 6871-6978 (2009) ("Liu").*
Chew et al., 3 Springer Plus, 1-7 (2014).*
L. Gianni et al., 31 Journal of Clinical Oncology, 1719-1725 (2013).*
T-C Chou et al., 58 Pharmacological Reviews, 621-681 (2006).*
T-C Chou, 70 Cancer Research, 440-446 (2010).*
Aldana-Masangkay (Nov. 7, 2011) "The Role of HDAC6 in Cancer," J. Biomed. Biotechnol. 2011:875824.
Bodo et al. (Oct. 2013) "The phosphatidylinositol 3-kinases (PI3K) inhibitor GS-1101 synergistically potentiates histone deacetylase inhibitor-induced proliferation inhibition and apoptosis through the inactivation of PI3K and extracellular signal-regulated kinase pathways," British Journal of Haematology. 163:72-80.
Delinger et al. (2005) "Inhibition of phosphatidylinositol 3-kinase/Akt and histone deacetylase activity induces apoptosis in non-small cell lung cancer in vitro and in vivo," The Journal of Thoracic and Cardiovascular Surgery. 130:1422-1429.
Rahmani et al. (2003) "Inhibition of PI-3 kinase sensitizes human leukemic cells to histone deacetylase inhibitor-mediated apoptosis through p44/42 MAP kinase inactivation and abrogation of p21CIP1/WAF1 induction rather than AKT inhibition," Oncogene. 22:6231-6242.
Turke (Jul. 15, 2010) "PIKing the right patient," Clin. Cancer Res. 16:3523-3525.
International Search Report with Written Opinion corresponding to International Patent Application No. PCT/US2014/059238, mailed Mar. 5, 2015.
International Search Report with Written Opinion corresponding to International Patent Application No. PCT/US2014/059640, mailed Mar. 12, 2015.
Butler et al. (2000) "Suberoylanilide Hydroxamic Acid, an Inhibitor of Histone Deacetylase, Suppresses the Growth of Prostate Cancer Cells in Vitro and in Vivo," Cancer Research. 60:5165-5170.
Costello et al. (Dec. 2012) "Evidence for Changes in RREB-1, ZIP3, and Zinc in the Early Development of Pancreatic Adenocarcinoma," J. Gastrointest. Canc. 43:570-578.
Dokmanovic et al. (2007) "Histone Deacetylase Inhibitors: Overview and Perspectives," Mol. Cancer Res. 5(10):981-989.
Giannini et al. (Jul. 2012) "Histone Deacetylase Inhibitors in the Treatment of Cancer: Overview and Perspectives," Future Med. Chem. 4(11):1439-1460.
Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.
Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.
Lane et al. (2009) "Histone Deacetylase Inhibitors in Cancer Therapy," J. Clin. Oncol. 27:5459-5468.
Loudni et al. (2007) "Design, synthesis and biological evaluation of 1,4-benzodiazepine-2, 5-dione-based HDAC inhibitors," Bioorganic and Medicinal Chemistry Letters. 17:4819-4823.
Mazitschek et al. (2008) "Development of a Fluorescence Polarization Based Assay for Histone Deacetylase Ligand Discovery," Bioorganic and Medicinal Chemistry Letters. 18(9):2809-2812.
Miller et al. (1998) "Paclitaxel as the Initial Treatment of Multiple Myeloma: An Eastern Cooperative Oncology Group Study (E1A93)," Am. J. Clin. Oncol. 21(6):553-556.
Perez (1998) "Paclitaxel in Breast Cancer," The Oncologist. 3:373-389.
Ropero et al. (2007) "The Role of Histone Deacetylases (HDACs) in Human Cancer," Molecular Oncology. 1:19-25.
Smil et al. (2009) "Novel HDAC6 Isoform Selective Chiral Small Molecule Histone Deacetylase Inhibitors," Bioorganic and Medicinal Chemistry Letters. 19:688-692.
Sporn et al. (2000) "Chemoprevention of Cancer," Carcinogenesis. 21(3):525-530.
Thoppil et al. (Sep. 2011) "Terpenoids as Potential Chemopreventive and Therapeutic Agents in Liver Cancer," World J. Hepatol. 3(9):228-249.
International Search Report with Written Opinion corresponding to International Patent Application No. PCT/US2011/021982, mailed Oct. 10, 2011.
Search Opinion corresponding to European Patent Application No. 11735212, dated Jun. 26, 2014.
Written Opinion corresponding to Singapore Patent Application No. Application No. 201205393-0, dated Nov. 15, 2013.
Angibaud et al. (2005) "Discovery of Pyrimidyl-5-hydroxamic acids as New Potent Histone Deacetylase Inhibitors," European Journal of Medicinal Chemistry. 40(6):597-606.
Brana et al. (2002) "Synthesis and biological evaluation of novel 2-(1H-imidazol-4-yl)cyclopropane carboxylic acids: key intermediates for H3 histamine receptor ligands," BioOrganic & Medicinal Chemistry Letter. 12(24):3561-3563.
Broxterman et al. (1992) "Synthesis of (optically active) sulfur-containing trifunctional amino acids by radical addition to (optically active) unsaturated amino acids," The Journal of Organic Chemistry. 57(23):6286-6294.
Carey et al. (2006) "Histone deacetylase inhibitors: gathering pace," Current Opinion in Pharmacology. 6:369-375.
Chuang et al. (2009) "Multiple roles of HDAC inhibition in neurodegenerative conditions," Trends in Neurosciences. 32(11):591-601.
Dallavalle et al. (2012) "Development and therapeutic impact of HDAC6-selective inhibitors," Biochemical Pharmacology. 84:756-765.
Elaut et al. (2007) "The Pharmaceutical Potential of Histone Deacetylase Inhibitors," Current Pharmaceutical Design. 13:2584-2620.
Foks et al. (1972) "Investigations on Pyrazine Derivatives Part II. Synthesis and Tuberculostatic Action of Some 6Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Neidle, Stephen: Ed. (2008) Cancer Drug Design and Discovery. Elsevier/Academic Press. pp. 427-431.
Pellicciari et al. (1996) "Synthesis and Pharmacological Characterization of All Sixteen Stereoisomers of 2-(2'-Carboxy-3'-

(56) References Cited

OTHER PUBLICATIONS phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist," Journal of Medicinal Chemistry. 39(11):2259-2269.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Walbrick et al.(1968) "A general method for synthesizing optically active 1,3-disubstituted allene hydrocarbons," The Journal of the American Chemical Society. 90(11):2895-2901.
Warner et al. (1992) "Electron demand in the transition state of the cyclopropylidene to allene ring opening," The Journal of Organic Chemistry. 57(23):6294-6300.
International Preliminary Report on Patentability corresponding to International Patent Application No. PCT/US2011/060791, dated Jul. 22, 2014.
International Search Report with Written Opinion corresponding to International Patent Application No. PCT/US2011/060791, mailed Mar. 5, 2014.
Supplementary European Search Report corresponding to European Application No. 11840803.8, dated Mar. 5, 2014.
U.S. Appl. No. 14/824,831, filed Aug. 12, 2015, John H. van Duzer.
U.S. Appl. No. 14/753,913, filed Jun. 29, 2015, John H. van Duzer.
U.S. Appl. No. 14/631,971, filed Feb. 26, 2015, Ralph Mazitschek.
U.S. Appl. No. 14/576,313, filed Dec. 19, 2014, Min Yang.
U.S. Appl. No. 14/878,536, filed Oct. 8, 2015, Jeffrey R. Shearstone.
U.S. Appl. No. 14/792,046, filed Jul. 6, 2015, Simon S. Jones.

* cited by examiner

A

B

COMBINATIONS OF HISTONE DEACETYLASE INHIBITORS AND EITHER HER2 INHIBITORS OR PI3K INHIBITORS

CROSS-REFERENCE TO RELATED APPLICATIONS

This application claims priority to U.S. Provisional Application Ser. No. 61/888,207, filed Oct. 8, 2013, which is incorporated herein by reference in its entirety.

BACKGROUND

Estrogen receptor (ER) and overexpressed Her2 are two major oncogenic proteins in hormone positive breast cancers. Current treatments to block ER or Her2 have been shown to effectively slow tumor growth. However, the need to overcome arising drug resistance has led to the development of combination and adjuvant drugs as new therapeutic approaches.

Phosphatidylinositide 3-kinases (PI 3-kinases, PI3Ks, PI(3)Ks, PI-3Ks, phosphatidylinositol-3-kinases, or phosphoinositide 3-kinases) are a family of enzymes involved in cellular functions, such as cell growth, proliferation, differentiation, motility, survival and intracellular trafficking, which in turn are involved in cancer. PI3Ks are a family of related intracellular signal transducer enzymes capable of phosphorylating the 3 position hydroxyl group of the inositol ring of phosphatidylinositol.

Histone deacetylase (HDAC) inhibition can cause breast cancer cell growth arrest, and has been reported to repress both ER and Her2 transcription. However, Class I HDAC inhibition leads to significant adverse effects and an alternative HDAC inhibition profile is desirable, particularly in combination with other therapeutic agents.

HDAC6 is a Class IIb HDAC and is known to remove acetyl groups from many cellular proteins, including α-tubulin and HSP90. It has been reported that HSP90 hyperacetylation destabilizes its target proteins, including ER and EGFR. Inhibitors of HDAC6 have demonstrated anti-cancer proliferative activity in various cancer types, including Her2+ breast cancer. Blocking HDAC6 activity has been shown to cause Her2+ breast cancer cell growth inhibition through various mechanisms, including destabilization of Her2 mRNA and protein.

Due to the dose-limiting toxicities of the non-selective HDAC inhibitors, there is an ongoing need in the art for more efficacious and less toxic compositions and methods for the treatment of breast cancer. In order to meet these needs, provided herein are pharmaceutical combinations comprising an HDAC inhibitor and either a Her2 inhibitor or a PI3K inhibitor, and methods for the treatment of breast cancer. The combinations and methods of the invention are well tolerated and do not exhibit the dose-limiting toxicities of prior therapies.

SUMMARY OF THE INVENTION

Provided herein are pharmaceutical combinations for the treatment of breast cancer in a subject in need thereof. Also provided herein are methods for treating breast cancer in a subject in need thereof.

Provided in some embodiments are combinations comprising a histone deacetylase (HDAC) inhibitor and a Her2 inhibitor for the treatment of breast cancer in a subject in need thereof. Provided in other embodiments are combinations comprising a histone deacetylase (HDAC) inhibitor and a PI3K inhibitor for the treatment of breast cancer in a subject in need thereof. Provided in other embodiments are combinations comprising a histone deacetylase (HDAC) inhibitor and doxorubicin for the treatment of breast cancer in a subject in need thereof.

Provided in some embodiments are methods for treating breast cancer in a subject in need thereof comprising administering to the subject an effective amount of a combination comprising a histone deacetylase (HDAC) inhibitor and a Her2 inhibitor. Provided in other embodiments are methods for treating breast cancer in a subject in need thereof comprising administering to the subject an effective amount of a combination comprising a histone deacetylase (HDAC) inhibitor and a PI3K inhibitor.

In some embodiments, the HDAC inhibitor is an HDAC6 specific inhibitor. In specific embodiments, the HDAC6 specific inhibitor is a compound of Formula I:

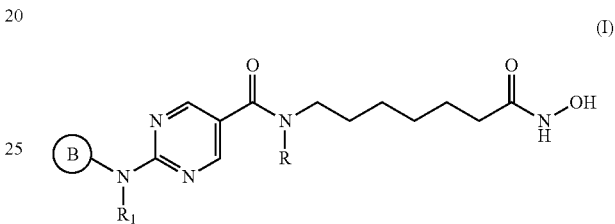

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl.

In preferred embodiments, the compound of Formula I is:

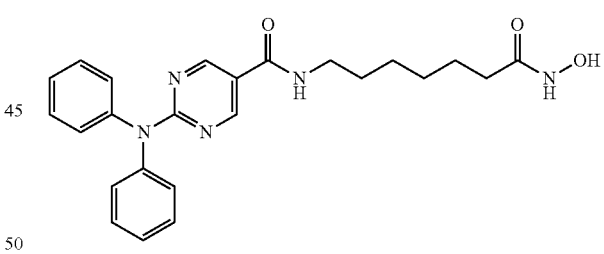

or a pharmaceutically acceptable salt thereof.

In yet other embodiments, the compound of Formula I is:

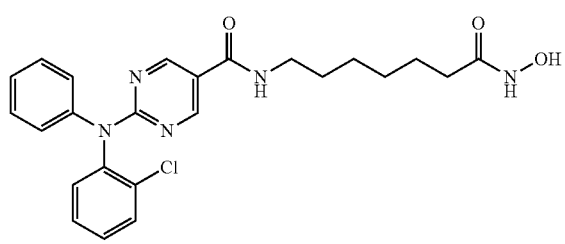 [SMILES: O=C(CCCCCCNC(=O)c1cnc(N(c2ccccc2)c2ccccc2Cl)nc1)NO]

or a pharmaceutically acceptable salt thereof.

In other specific embodiments, the HDAC6 specific inhibitor is a compound of Formula II:

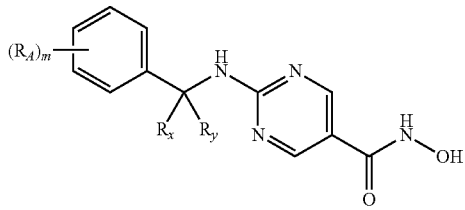

or a pharmaceutically acceptable salt thereof,
wherein,
$R_x$ and $R_y$ together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2.

In preferred embodiments, the compound of Formula II is:

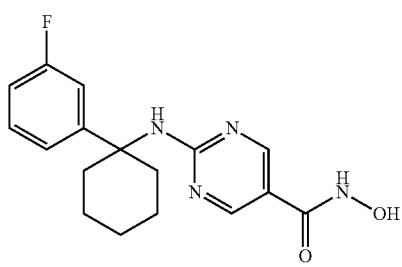 [SMILES: O=C(NO)c1cnc(NC2(c3cccc(F)c3)CCCCC2)nc1]

or a pharmaceutically acceptable salt thereof.

In other preferred embodiments, the compound of Formula II is:

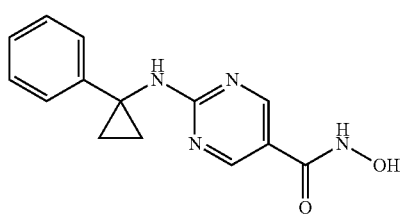 [SMILES: O=C(NO)c1cnc(NC2(c3ccccc3)CC2)nc1]

or a pharmaceutically acceptable salt thereof.

In specific embodiments, the Her2 inhibitor is lapatinib or pharmaceutically acceptable salts thereof.

In specific embodiments, the PI3K inhibitor is IPI-145, GDC-0941, or CAL-101, or pharmaceutically acceptable salts thereof.

In some embodiments, the HDAC inhibitor and the Her2 inhibitor are administered with a pharmaceutically acceptable carrier. In other embodiments, the HDAC inhibitor and the PI3K inhibitor are administered with a pharmaceutically acceptable carrier.

In some embodiments, the HDAC inhibitor and the Her2 inhibitor are administered in separate dosage forms. In other embodiments, the HDAC inhibitor and the Her2 inhibitor are administered in a single dosage form.

In some embodiments, the HDAC inhibitor and the PI3K inhibitor are administered in separate dosage forms. In other embodiments, the HDAC inhibitor and the PI3K inhibitor are administered in a single dosage form.

In some embodiments, the HDAC inhibitor and the Her2 inhibitor are administered at different times. In other embodiments, the HDAC inhibitor and the Her2 inhibitor are administered at substantially the same time.

In some embodiments, the HDAC inhibitor and the PI3K inhibitor are administered at different times. In other embodiments, the HDAC inhibitor and the PI3K inhibitor are administered at substantially the same time.

In some embodiments, the combination of the HDAC inhibitor and the Her2 inhibitor achieves a synergistic effect in the treatment of the subject in need thereof. In other embodiments, the combination of the HDAC inhibitor and the PI3K inhibitor achieves a synergistic effect in the treatment of the subject in need thereof.

In some embodiments of the combinations and/or methods, the HDAC6 specific inhibitor is a compound of Formula I:

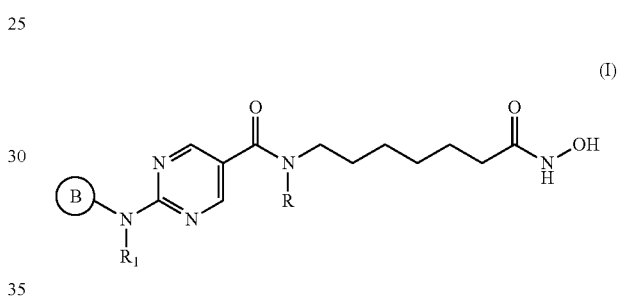

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl; and
the Her2 inhibitor is any Her2 inhibitor.

In specific embodiments of the combinations and/or methods, the HDAC6 specific inhibitor is:

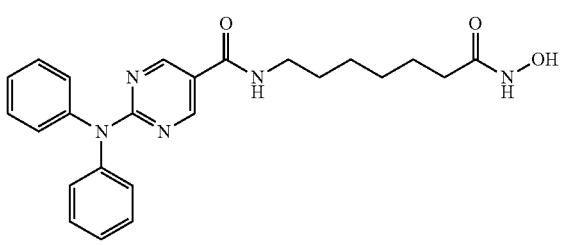 [SMILES: O=C(CCCCCCNC(=O)c1cnc(N(c2ccccc2)c2ccccc2)nc1)NO]

or a pharmaceutically acceptable salt thereof; and
the Her2 inhibitor is lapatinib or a pharmaceutically acceptable salt thereof.

In specific embodiments of the combinations and/or methods, the HDAC6 specific inhibitor is:

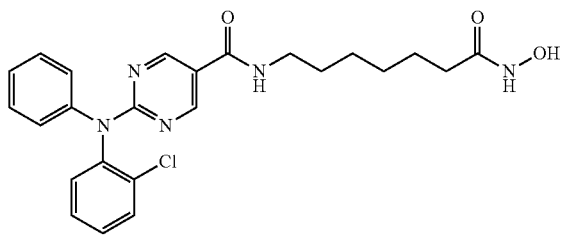 [SMILES: O=C(CCCCCCNC(=O)c1cnc(N(c2ccccc2)c2ccccc2Cl)nc1)NO]

or a pharmaceutically acceptable salt thereof; and the Her2 inhibitor is lapatinib or a pharmaceutically acceptable salt thereof.

In some embodiments of the combinations and/or methods, the HDAC6 specific inhibitor is a compound of Formula II:

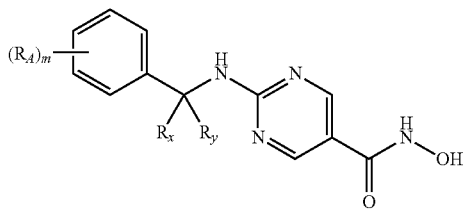

(II)

or a pharmaceutically acceptable salt thereof, wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2; and the Her2 inhibitor is any Her2 inhibitor.

In specific embodiments of the combinations and/or methods, the HDAC6 specific inhibitor is:

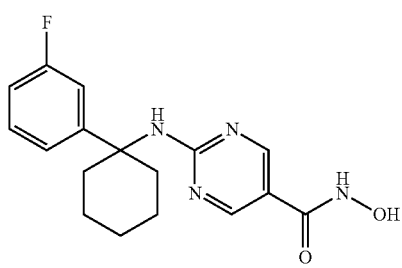 [SMILES: O=C(NO)c1cnc(NC2(c3cccc(F)c3)CCCCC2)nc1]

or a pharmaceutically acceptable salt thereof; and the Her2 inhibitor is lapatinib or a pharmaceutically acceptable salt thereof.

In specific embodiments of the combinations and/or methods, the HDAC6 specific inhibitor is:

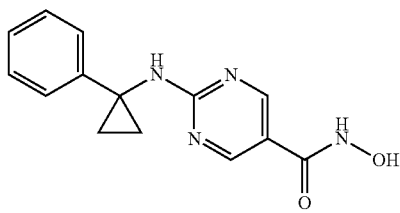 [SMILES: O=C(NO)c1cnc(NC2(c3ccccc3)CC2)nc1]

or a pharmaceutically acceptable salt thereof; and the Her2 inhibitor is lapatinib or a pharmaceutically acceptable salt thereof.

In some embodiments of the combinations and/or methods, the HDAC6 specific inhibitor is a compound of Formula I:

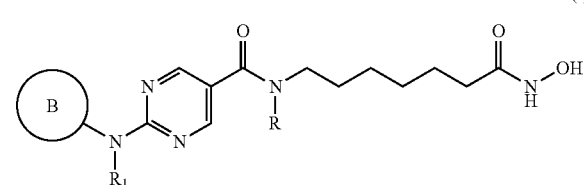

(I)

or a pharmaceutically acceptable salt thereof, wherein, ring B is aryl or heteroaryl;

$R_1$ is an aryl or heteroaryl, each of which may be optionally substituted by OH, halo, or $C_{1-6}$-alkyl; and R is H or $C_{1-6}$-alkyl; and the PI3K inhibitor is any PI3K inhibitor.

In specific embodiments of the combinations and/or methods, the HDAC6 specific inhibitor is:

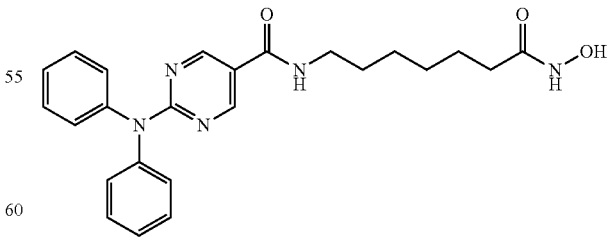

or a pharmaceutically acceptable salt thereof; and the PI3K inhibitor is selected from the group consisting of IPI-145, GDC-0941, and CAL-101, or a pharmaceutically acceptable salt thereof.

In specific embodiments of the combinations and/or methods, the HDAC6 specific inhibitor is:

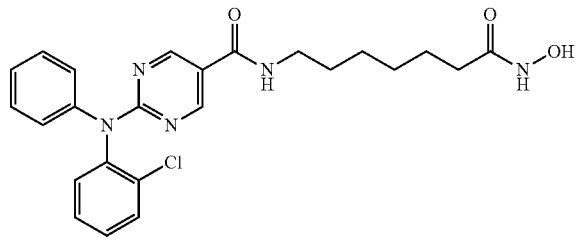 [SMILES: O=C(CCCCCCNC(=O)c1cnc(N(c2ccccc2)c2ccccc2Cl)nc1)NO]

or a pharmaceutically acceptable salt thereof; and the PI3K inhibitor is selected from the group consisting of IPI-145, GDC-0941, and CAL-101, or a pharmaceutically acceptable salt thereof.

In some embodiments of the combinations and/or methods, the HDAC6 specific inhibitor is a compound of Formula II:

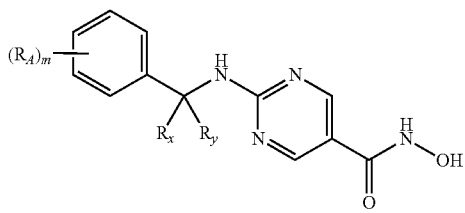

(II)

or a pharmaceutically acceptable salt thereof, wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2; and the PI3K inhibitor is any PI3K inhibitor.

In specific embodiments of the combinations and/or methods, the HDAC6 specific inhibitor is:

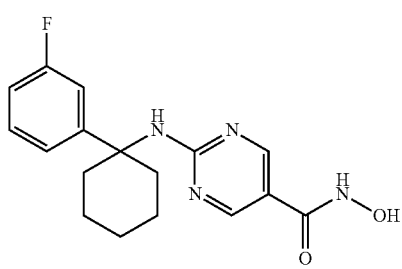 [SMILES: O=C(NO)c1cnc(NC2(c3cccc(F)c3)CCCCC2)nc1]

or a pharmaceutically acceptable salt thereof; and the PI3K inhibitor is selected from the group consisting of IPI-145, GDC-0941, and CAL-101, or a pharmaceutically acceptable salt thereof.

In specific embodiments of the combinations and/or methods, the HDAC6 specific inhibitor is:

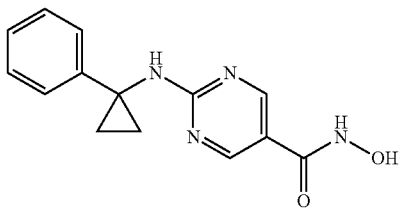 [SMILES: O=C(NO)c1cnc(NC2(c3ccccc3)CC2)nc1]

or a pharmaceutically acceptable salt thereof; and the PI3K inhibitor is selected from the group consisting of IPI-145, GDC-0941, and CAL-101, or a pharmaceutically acceptable salt thereof.

Provided in some embodiments are methods for inhibiting migration and/or invasion of a breast cancer cell in a subject in need thereof comprising administering to the subject a therapeutically effective amount of a histone deacetylase 6 (HDAC6) specific inhibitor or a pharmaceutically acceptable salt thereof. The HDAC6 specific inhibitor may be any compound selected from the group consisting of Compound A, Compound B, Compound C, and Compound D.

Other objects, features, and advantages will become apparent from the following detailed description. The detailed description and specific examples are given for illustration only because various changes and modifications within the spirit and scope of the invention will become apparent to those skilled in the art from this detailed description. Further, the examples demonstrate the principle of the invention.

BRIEF DESCRIPTION OF THE FIGURES

FIG. 1A shows the $IC_{50}$ values for GDC-0941 at 0.05, 0.16, 0.5, 1.6, 5, and 16 μM of Compound A. FIG. 1B shows the $IC_{50}$ values for GDC-0941 at 1.3, 4, and 12 μM of Compound A. FIG. 1C shows the $IC_{50}$ values for GDC-0941 at 1.3, 4, and 12 μM of Compound C. FIG. 1D shows the $IC_{50}$ values for GDC-0941 at 0.5, 1.6, and 5 μM of Compound C.

In FIG. 3A, there was no pre-treatment with HDAC6 inhibitor. On the other hand, in FIG. 3B, there was pre-treatment with HDAC inhibitor, as HDAC6 inhibitors take time to act. In both assays, Tubastatin A, Compound C, and Compound A were given in concentrations in which the drugs are HDAC6 selective inhibitors. Gefitinib is an EGFR inhibitor. Equal variance two-sample two-tailed t-test, normalized against DMSO+EGF group. ** means $P<0.01$, * means $P<0.05$.

In FIG. 5A, * means P<0.001,  means P<0.01, and * means P<0.05. In FIG. 5B, * means P<0.05.

DETAILED DESCRIPTION

Figure 1:
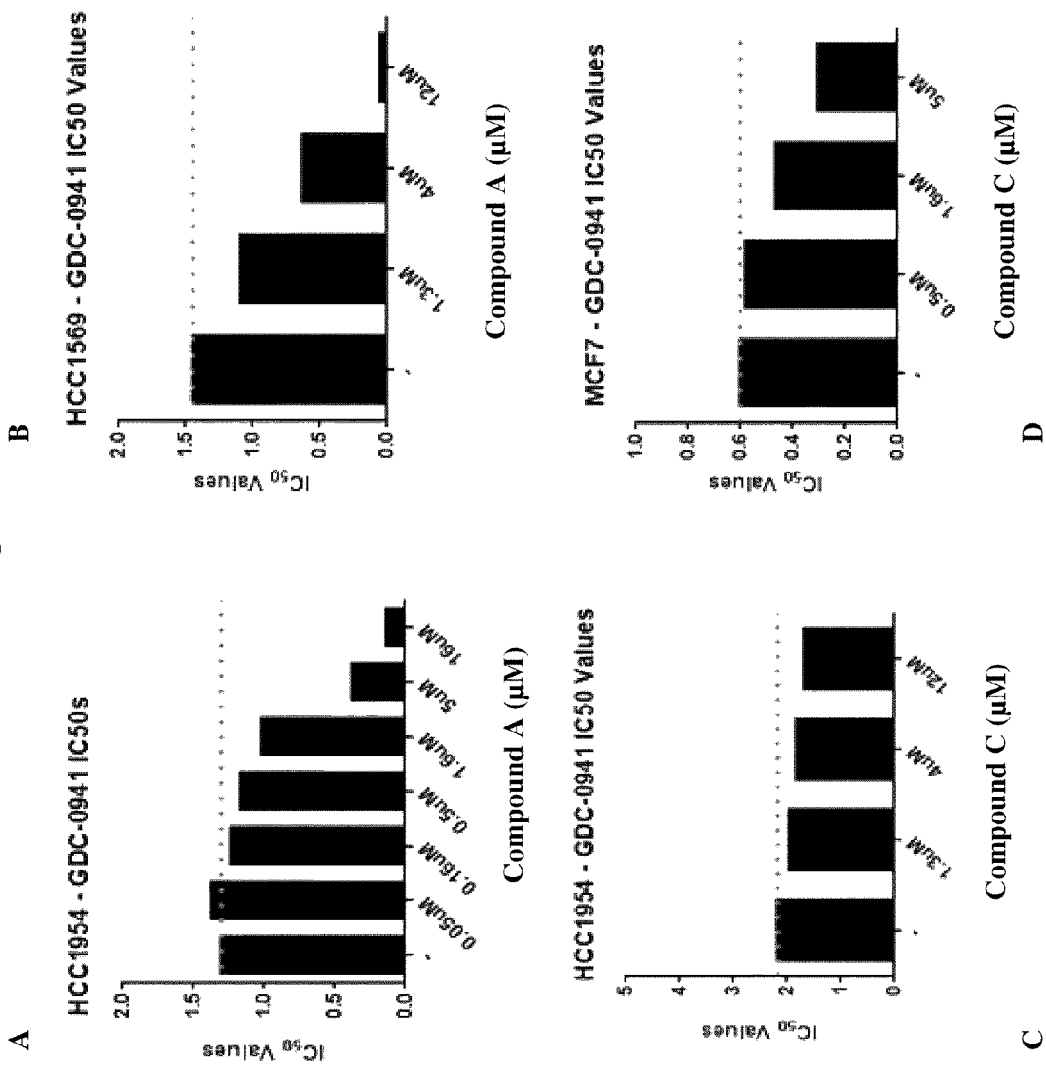
FIGS. 1A-D are a set of four graphs that show that the PI3K inhibitor GDC-0941 is potentiated by HDAC6 specific (selective) inhibitors.
Figure 2:
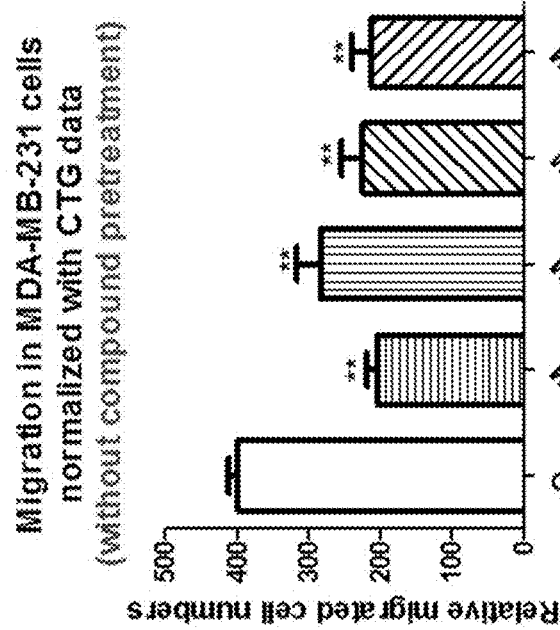
FIGS. 2A-B are a pair of graphs that show the results of migration assays in A549 cells (lung cancer cells) (FIG. 2A) and MDA-MB-231 cells (breast cancer cells) (FIG. 2B) in which no EGF was used to stimulate cancer cell migration. In both assays, there was no pre-treatment with HDAC6 inhibitor. In both assays, Tubastatin A, Compound C, and Compound A were given in concentrations in which the drugs are HDAC6 selective inhibitors. Gefitinib is an EGFR inhibitor. ** means $P<0.01$.
Figure 2:
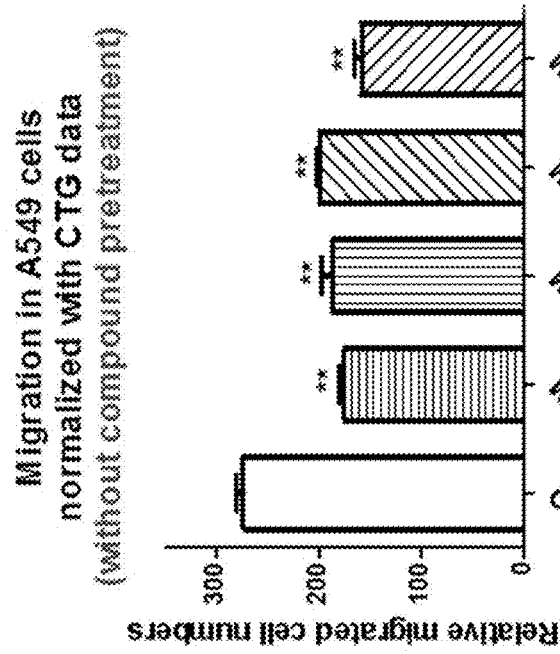
Figure 3:
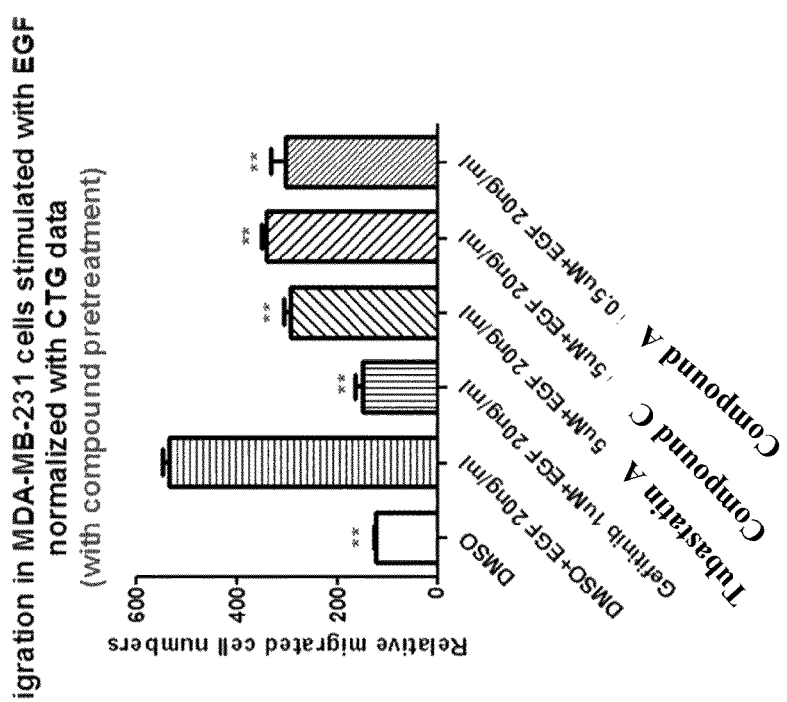
FIGS. 3A-B are a pair of graphs that show the results of migration assays in A549 cells (lung cancer cells) (FIG. 3A) and MDA-MB-231 cells (breast cancer cells) (FIG. 3B) in which EGF was used to stimulate cancer cell migration.
Figure 3:
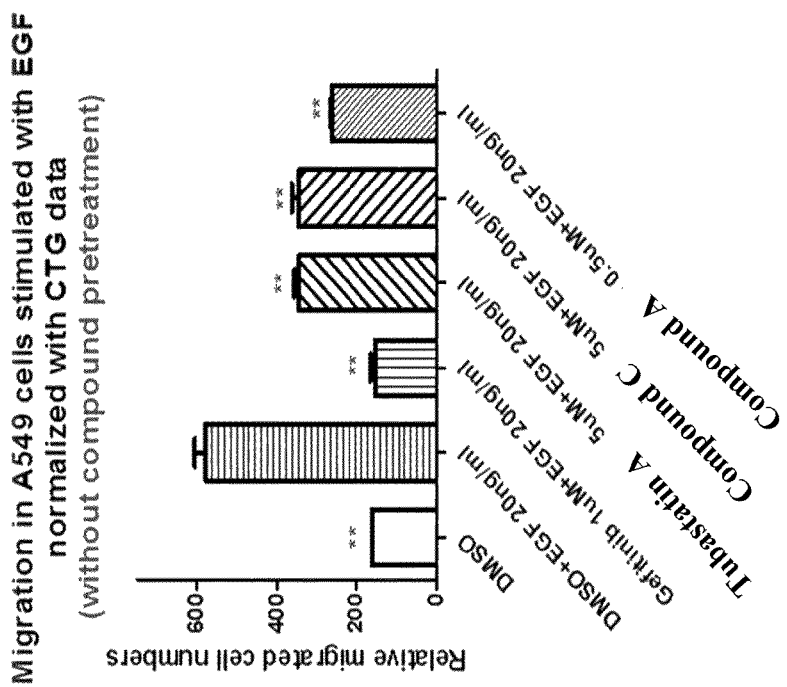
Figure 4:
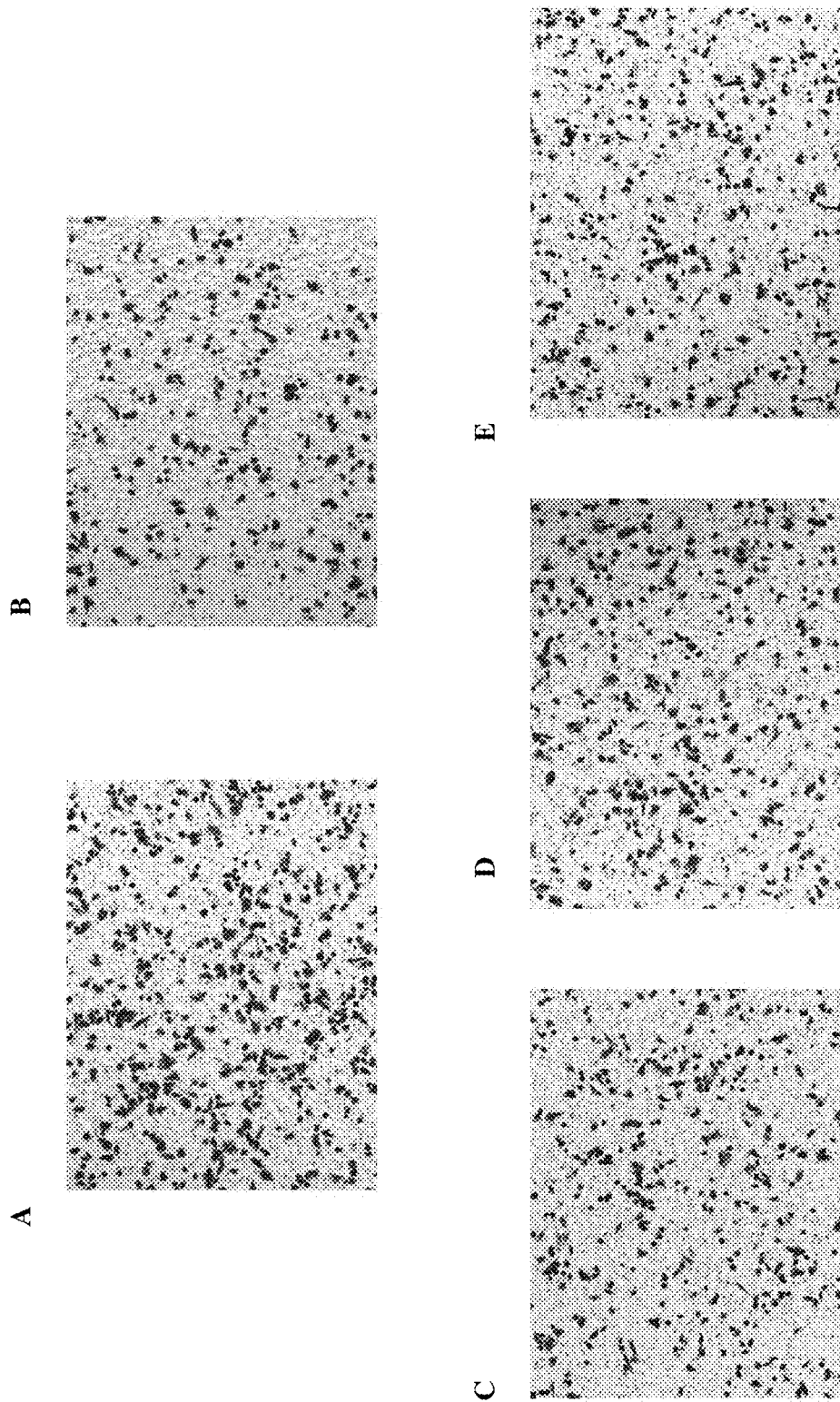
FIGS. 4A-E are a set of photographs that show MDA-MB-231 migration in DMSO (FIG. 4A), 1 μM Gefitinib (FIG. 4B), 5 μM Compound C (FIG. 4C), 5 μM Tubastatin A (FIG. 4D), and 0.5 μM Compound A (FIG. 4E). Gefitinib is an EGFR inhibitor.

The instant application is directed, generally, to combinations comprising a histone deacetylase (HDAC) inhibitor and a Her2 inhibitor, and methods for the treatment of breast cancer. The instant application is also directed, generally, to combinations comprising a histone deacetylase (HDAC) inhibitor and a PI3K inhibitor, and methods for the treatment of breast cancer.

DEFINITIONS

Listed below are definitions of various terms used to describe this invention. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkoxy" refers to an —O-alkyl moiety.

The terms "cycloalkyl" or "cycloalkylene" denote a monovalent group derived from a monocyclic or polycyclic saturated or partially unsaturated carbocyclic ring compound. Examples of $C_{3-8}$-cycloalkyl include, but not limited to, cyclopropyl, cyclobutyl, cyclopentyl, cyclohexyl, cyclopentyl and cyclooctyl; and examples of $C_{3-12}$-cycloalkyl include, but not limited to, cyclopropyl, cyclobutyl, cyclopentyl, cyclohexyl, bicyclo[2.2.1]heptyl, and bicyclo[2.2.2]octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "combination" refers to two or more therapeutic agents to treat a therapeutic condition or disorder described in the present disclosure. Such combination of therapeutic agents may be in the form of a single pill, capsule, or intravenous solution. However, the term "combination" also encompasses the situation when the two or more therapeutic agents are in separate pills, capsules, or intravenous solutions. Likewise, the term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "heteroaryl" refers to a mono- or poly-cyclic (e.g., bi-, or tri-cyclic or more) fused or non-fused, moieties or ring system having at least one aromatic ring, having from five to ten ring atoms of which one ring atom is selected from S, O, and N; zero, one or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "halo" refers to a halogen, such as fluorine, chlorine, bromine, and iodine.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6 specific" means that the compound binds to HDAC6 to a substantially greater extent, such as 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6 specific. On the other hand, a compound that binds to HDAC6 with an $IC_{50}$ of 50 nM and to HDAC1 with an $IC_{50}$ of 60 nM is not HDAC6 specific The term "inhibitor" is synonymous with the term antagonist.

Histone Deacetylase (HDAC) Inhibitors

Provided herein are pharmaceutical combinations for the treatment of breast cancer in a subject in need thereof. Also provided herein are methods for treating breast cancer in a subject in need thereof.

The combinations and methods of the invention comprise a histone deacetylase (HDAC) inhibitor. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6 specific inhibitor.

In some embodiments, the HDAC6 specific inhibitor is a compound of Formula I:

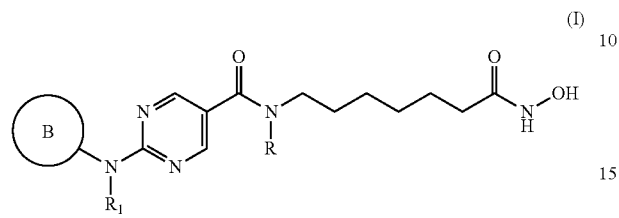

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl.
Representative compounds of Formula I include, but are not limited to:

Compound A

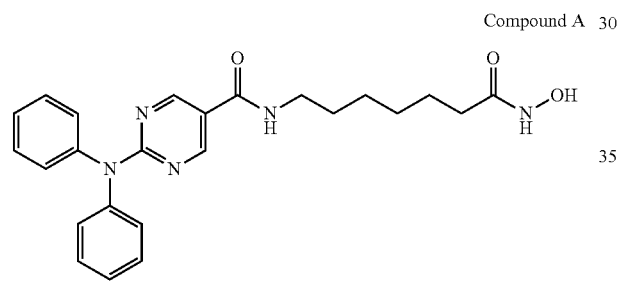

2-(diphenylamino)-N-(7-(hydroxyamino)-7-oxoheptyl)pyrimidine-5-carboxamide
$IC_{50}$(nM) HDAC6 = 10 HDAC3 = 84

Compound B

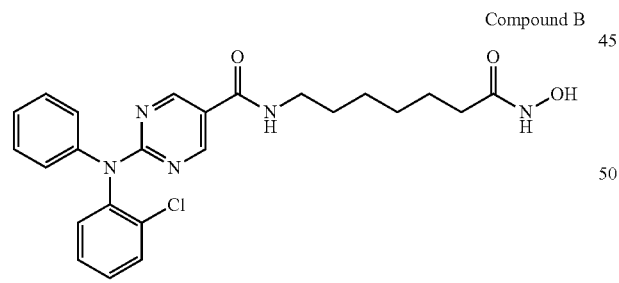

2-((2-chlorophenyl)(phenyl)amino)-N-(7-(hydroxyamino)-7-oxoheptyl)pyrimidine-5-carboxamide
$IC_{50}$(nM) HDAC6 = 4 HDAC3 = 76 or pharmaceutically acceptable salts thereof.

The preparation and properties of selective HDAC6 inhibitors according to Formula I are provided in International Patent Application No. PCT/US2011/021982, the entire contents of which is incorporated herein by reference.

In other embodiments, the HDAC6 specific inhibitor is a compound of Formula II:

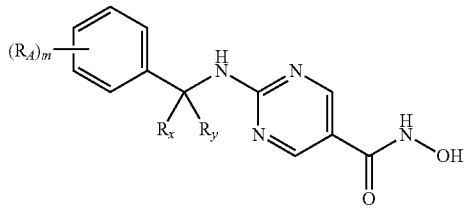

(II)

or a pharmaceutically acceptable salt thereof,
wherein,
$R_x$ and $R_y$ together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2.
Representative compounds of Formula II include, but are not limited to:

Compound C

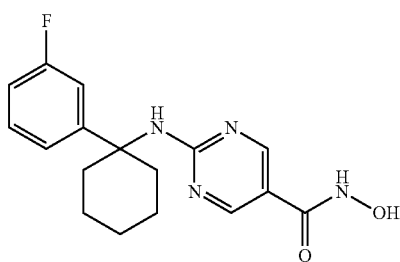

$IC_{50}$(nM) HDAC6 = 7 HDAC1 = 2123
HDAC2 = 2570 HDAC3 = 11223

Compound D

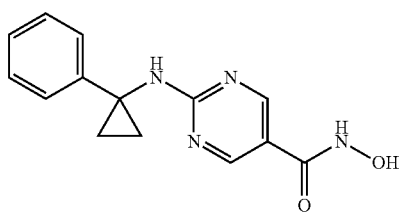

$IC_{50}$(nM) HDAC6 = 2 HDAC1 = 94
HDAC2 = 18 HDAC3 = 219 or pharmaceutically acceptable salts thereof.

The preparation and properties of selective HDAC6 inhibitors according to Formula II are provided in International Patent Application No. PCT/US2011/060791, the entire contents of which are incorporated herein by reference.

In some embodiments, the compounds described herein are unsolvated. In other embodiments, one or more of the compounds are in solvated form. As known in the art, the solvate can be any of pharmaceutically acceptable solvent, such as water, ethanol, and the like.

Her2 Inhibitors

Some embodiments of the combinations and methods of the invention comprise a Her2 inhibitor. The Her2 inhibitor may be any Her2 inhibitor. Examples of Her2 inhibitors, include, but are not limited to, lapatinib, trastuzumab, pertuzumab, NeuVax, cetuximab, and tyrosine kinase inhibitors. Preferably, the Her2 inhibitor is lapatinib or a pharmaceutically acceptable salt thereof.

In some embodiments, the compounds described herein are unsolvated. In other embodiments, one or more of the compounds are in solvated form. As known in the art, the solvate can be any of pharmaceutically acceptable solvent, such as water, ethanol, and the like.

Phosphoinositide 3-kinase (PI3K) Inhibitors

Some embodiments of the combinations and methods of the invention comprise a PI3K inhibitor. The PI3K inhibitor may be any PI3K inhibitor. Examples of PI3K inhibitors, include, but are not limited to, Wortmannin, demethoxyviridin, LY294002, perifosine, CAL-101, PX-866, IPI-145, BAY 80-6946, BEZ-235, RP-6503, TGR 1202, SF-1126, INK-1117, GDC-0941, BKM-120, XL-147, XL-765, Palomid 529, GSK-1059615, ZSTK-474, PWT-33597, IC-87114, TG100-115, CAL-263, RP-6530, PI-103, GNE-477, CUDC-907, and AEZS-136. Preferably, the PI3K inhibitor is selected from the group consisting of IPI-145, GDC-0941, and CAL-101, or a pharmaceutically acceptable salt thereof.

In some embodiments, the compounds described herein are unsolvated. In other embodiments, one or more of the compounds are in solvated form. As known in the art, the solvate can be any of pharmaceutically acceptable solvent, such as water, ethanol, and the like.

Combinations/Pharmaceutical Combinations

Provided herein are combinations for the treatment of breast cancer in a subject in need thereof. Provided in some embodiments are combinations comprising a histone deacetylase (HDAC) inhibitor and a Her2 inhibitor for the treatment of breast cancer in a subject in need thereof. Provided in other embodiments are combinations comprising a histone deacetylase (HDAC) inhibitor and a PI3K inhibitor for the treatment of breast cancer in a subject in need thereof.

In some embodiments of the combinations, the HDAC inhibitor is an HDAC6 specific inhibitor. In specific embodiments, the HDAC6 specific inhibitor is a compound of Formula I:

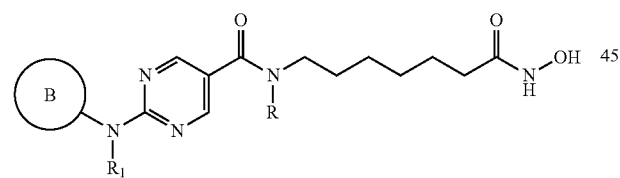

(I)

or a pharmaceutically acceptable salt thereof.

In preferred embodiments, the compound of Formula I is:

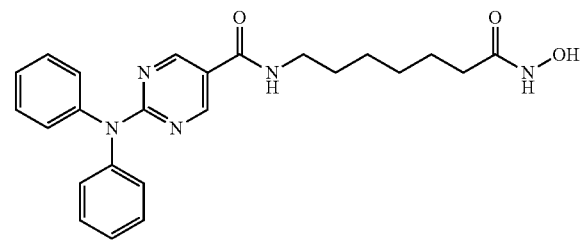 [SMILES: O=C(CCCCCCNC(=O)c1cnc(N(c2ccccc2)c2ccccc2)nc1)NO]

or a pharmaceutically acceptable salt thereof.

In yet other embodiments, the compound of Formula I is:

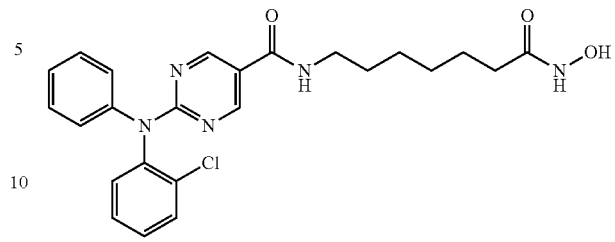

or a pharmaceutically acceptable salt thereof.

In other specific embodiments, the HDAC6 specific inhibitor is a compound of Formula II:

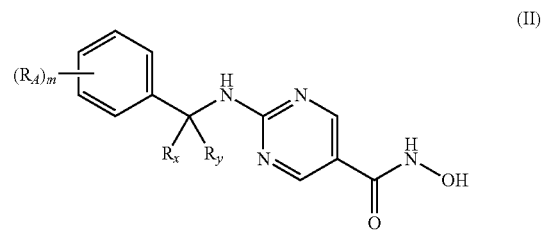

(II)

or a pharmaceutically acceptable salt thereof.

In preferred embodiments, the compound of Formula II is:

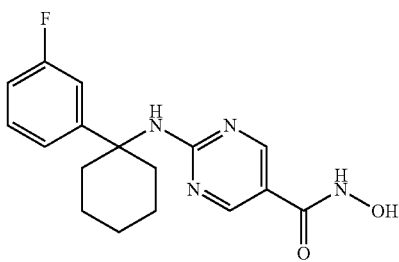 [SMILES: O=C(NO)c1cnc(NC2(c3cccc(F)c3)CCCCC2)nc1]

or a pharmaceutically acceptable salt thereof.

In other preferred embodiments, the compound of Formula II is:

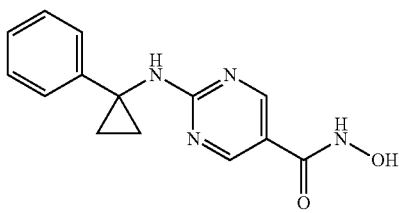 [SMILES: O=C(NO)c1cnc(NC2(c3ccccc3)CC2)nc1]

or a pharmaceutically acceptable salt thereof.

In some embodiments of the combinations, the Her2 inhibitor is any Her2 inhibitor or a pharmaceutically acceptable salt thereof. In preferred embodiments, the Her2 inhibitor is lapatinib or a pharmaceutically acceptable salt thereof.

In other embodiments of the combinations, the PI3K inhibitor is any PI3K inhibitor or a pharmaceutically acceptable salt thereof. In preferred embodiments, the PI3K inhibitor is selected from the group consisting of IPI-145, GDC-0941, and CAL-101, or a pharmaceutically acceptable salt thereof.

In one embodiment, provided herein is a combination therapy comprising an HDAC6 specific inhibitor and a Her2 inhibitor, wherein the HDAC6 specific inhibitor is a compound of Formula I:

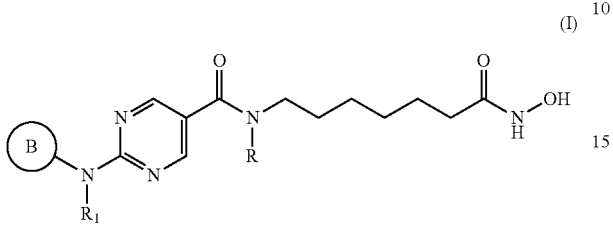

(I)

or a pharmaceutically acceptable salt thereof,
wherein,
ring B is aryl or heteroaryl;
$R_1$ is an aryl or heteroaryl, each of which may be optionally substituted by OH,
halo, or $C_{1-6}$-alkyl; and
R is H or $C_{1-6}$-alkyl; and
the Her2 inhibitor is any Her2 inhibitor.

In specific embodiments of the combinations, the HDAC6 specific inhibitor is:

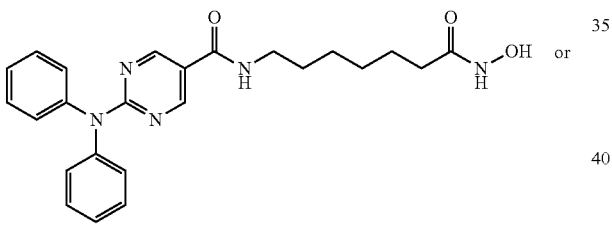

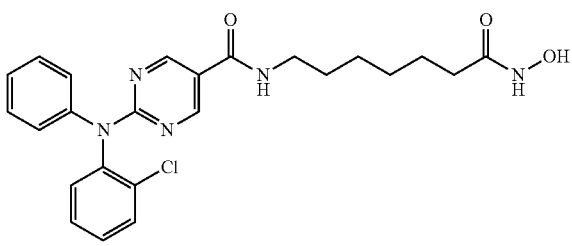

or pharmaceutically acceptable salts thereof; and
the Her2 inhibitor is lapatinib or a pharmaceutically acceptable salt thereof.

In another embodiment, provided herein is a combination therapy comprising an HDAC6 specific inhibitor and a Her2 inhibitor, wherein the HDAC6 specific inhibitor is a compound of Formula II:

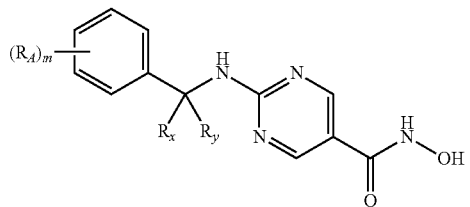

(II)

or a pharmaceutically acceptable salt thereof,
wherein,
$R_x$ and $R_y$, together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2; and
the Her2 inhibitor is any Her2 inhibitor.

In specific embodiments of the combinations, the HDAC6 specific inhibitor is:

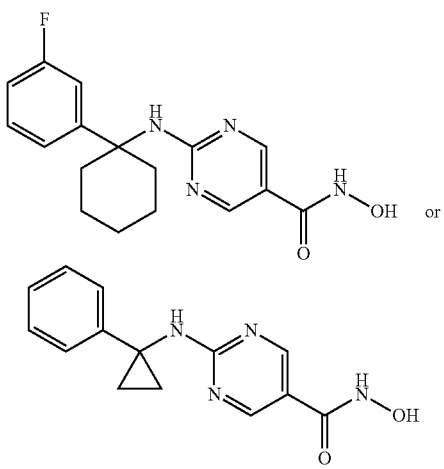

or a pharmaceutically acceptable salt thereof; and
the Her2 inhibitor is lapatinib or a pharmaceutically acceptable salt thereof.

In one embodiment, provided herein is a combination therapy comprising an HDAC6 specific inhibitor and a PI3K inhibitor, wherein the HDAC6 specific inhibitor is a compound of Formula I:

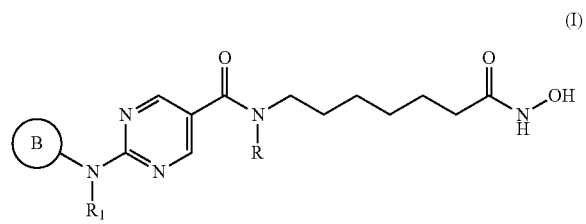

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;

and

R is H or $C_{1-6}$-alkyl; and the PI3K inhibitor is any PI3K inhibitor.

In specific embodiments of the combinations, the HDAC6 specific inhibitor is:

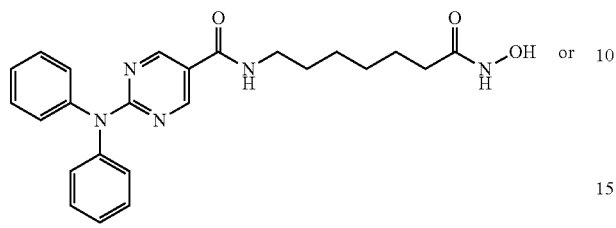

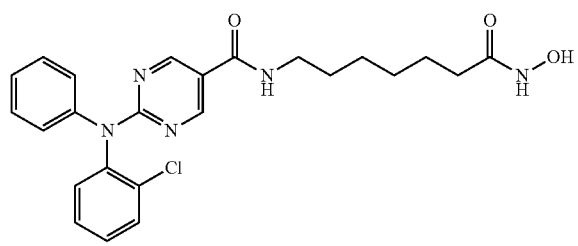

or pharmaceutically acceptable salts thereof; and the PI3K inhibitor is selected from the group consisting of IPI-145, GDC-0941, and CAL-101, or a pharmaceutically acceptable salt thereof.

In another embodiment, provided herein is a combination therapy comprising an HDAC6 specific inhibitor and a PI3K inhibitor, wherein the HDAC6 specific inhibitor is a compound of Formula II:

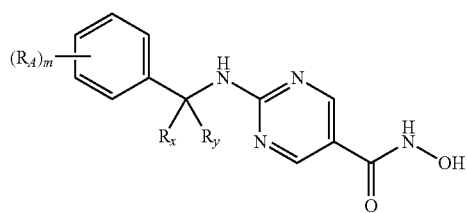

(II)

or a pharmaceutically acceptable salt thereof, wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2; and the PI3K inhibitor is any PI3K inhibitor.

In specific embodiments of the combinations, the HDAC6 specific inhibitor is:

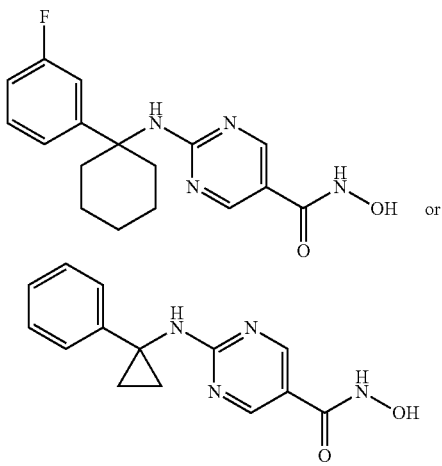

or a pharmaceutically acceptable salt thereof; and the PI3K inhibitor is selected from the group consisting of IPI-145, GDC-0941, and CAL-101, or a pharmaceutically acceptable salt thereof.

Although the compounds of Formulas I and II are depicted in their neutral forms, in some embodiments, these compounds are used in a pharmaceutically acceptable salt form. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Administration/Dose

In some embodiments, the HDAC inhibitor (a compound of Formula I or II) is administered simultaneously with either the Her2 inhibitor or PI3K inhibitor. Simultaneous administration typically means that both compounds enter the patient at precisely the same time. However, simultaneous administration also includes the possibility that the HDAC inhibitor and either the Her2 inhibitor or PI3K inhibitor enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the combination of compounds. In another example, simultaneous administration of separate solutions, one of which contains the HDAC inhibitor and the other of which contains either the Her2 inhibitor or PI3K inhibitor, can be employed. In one example wherein the compounds are in solid form, simultaneous administration can be achieved by administering a composition containing the combination of compounds. Alternatively, simultaneous administration can be achieved by administering two separate compositions, one comprising the HDAC inhibitor and the other comprising either the Her2 inhibitor or PI3K inhibitor.

In other embodiments, the HDAC inhibitor and either the Her2 inhibitor or PI3K inhibitor are not administered simultaneously. In some embodiments, the HDAC inhibitor is administered before either the Her2 inhibitor or PI3K inhibitor. In other embodiments, either the Her2 inhibitor or PI3K inhibitor is administered before the HDAC inhibitor. The time difference in non-simultaneous administrations can be greater than 1 minute, five minutes, 10 minutes, 15 minutes, 30 minutes, 45 minutes, 60 minutes, two hours, three hours, six hours, nine hours, 12 hours, 24 hours, 36 hours, or 48 hours. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, one or both of the HDAC inhibitor and either the Her2 inhibitor or PI3K inhibitor are administered in a therapeutically effective amount or dosage. A "therapeutically effective amount" is an amount of HDAC6 inhibitor (a compound of Formula I or II) or either a Her2 inhibitor or PI3K inhibitor that, when administered to a patient by itself, effectively treats the breast cancer. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the HDAC inhibitor and either the Her2 inhibitor or PI3K inhibitor are administered in a sub-therapeutically effective amount or dosage. A sub-therapeutically effective amount is an amount of HDAC inhibitor (a compound of Formula I or II) or either a Her2 inhibitor or PI3K inhibitor that, when administered to a patient by itself, does not completely inhibit over time the biological activity of the intended target.

Whether administered in therapeutic or sub-therapeutic amounts, the combination of the HDAC inhibitor and either the Her2 inhibitor or PI3K inhibitor should be effective in treating breast cancer. For example, a sub-therapeutic amount of a compound of Her2 inhibitor or PI3K inhibitor can be an effective amount if, when combined with a compound of Formula I or II (HDAC inhibitor), the combination is effective in the treatment of breast cancer.

In some embodiments, the combination of compounds exhibits a synergistic effect (i.e., greater than additive effect) in the treatment of the breast cancer. The term "synergistic effect" refers to the action of two agents, such as, for example, a HDAC inhibitor and either a Her2 inhibitor or PI3K inhibitor, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In preferred embodiments of the invention, the combinations and methods include an HDAC inhibitor of Formula II and either a Her2 inhibitor or a PI3K inhibitor. Thus, in one embodiment, the combinations and methods include Compound C and a Her2 inhibitor. In another embodiment, the combinations and methods include Compound C and a PI3K inhibitor. In another embodiment, the combinations and methods include Compound D and a Her2 inhibitor. In another embodiment, the combinations and methods include Compound D and a PI3K inhibitor. These embodiments exhibit synergy (also called potentiation in the Examples) such that sub-therapeutic amounts of the HDAC inhibitor of Formula II may be used.

In different embodiments, depending on the combination and the effective amounts used, the combination of compounds can inhibit breast cancer growth, achieve breast cancer stasis, or even achieve substantial or complete breast cancer regression.

While the amounts of a HDAC inhibitor and either a Her2 inhibitor or PI3K inhibitor should result in the effective treatment of breast cancer, the amounts, when combined, are preferably not excessively toxic to the patient (i.e., the amounts are preferably within toxicity limits as established by medical guidelines). In some embodiments, either to prevent excessive toxicity and/or provide a more efficacious treatment of breast cancer, a limitation on the total administered dosage is provided. Typically, the amounts considered herein are per day; however, half-day and two-day or three-day cycles also are considered herein.

Different dosage regimens may be used to treat breast cancer. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day. In some embodiments, each dosage contains both an HDAC inhibitor and either a Her2 inhibitor or PI3K inhibitor to be delivered as a single dosage, while in other embodiments, each dosage contains either a HDAC inhibitor and either a Her2 inhibitor or PI3K inhibitor to be delivered as separate dosages.

Compounds of Formula I and II, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC inhibitor and either the Her2 inhibitor or PI3K inhibitor of the pharmaceutical combination can be administered in a single unit dose or separate dosage forms. Accordingly, the phrase "pharmaceutical combination" includes a combination of two drugs in either a single dosage form or separate dosage forms, i.e., the pharmaceutically acceptable carriers and excipients described throughout the application can be combined with an HDAC inhibitor and either a Her2 inhibitor or PI3K inhibitor in a single unit dose, as well as individually combined with a HDAC inhibitor and either a Her2 inhibitor or PI3K inhibitor when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC inhibitors or Her2 inhibitors or PI3K inhibitors described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Methods of the Invention

The invention relates to methods for treating breast cancer in a subject in need thereof comprising administering to the subject a pharmaceutical combination of the invention. Thus, provided herein are methods for treating breast cancer in a subject in need thereof comprising administering to the subject a therapeutically effective amount of a combination comprising an HDAC inhibitor and a Her2 inhibitor. Also, provided herein are methods for treating breast cancer in a subject in need thereof comprising administering to the subject a therapeutically effective amount of a combination comprising an HDAC inhibitor and a PI3K inhibitor. Further, provided herein are methods for treating breast cancer in a subject in need thereof comprising administering to the subject a therapeutically effective amount of a combination comprising a histone deacetylase (HDAC) inhibitor and doxorubicin.

The subject considered herein is typically a human. However, the subject can be any mammal for which treatment is desired. Thus, the methods described herein can be applied to both human and veterinary applications.

The terms "treating" or "treatment" indicates that the method has, at the least, mitigated abnormal cellular proliferation. For example, the method can reduce the rate of breast cancer growth in a patient, or prevent the continued growth or spread of the breast cancer, or even reduce the overall reach of the breast cancer.

As such, in one embodiment, provided herein is a method for treating breast cancer in a subject in need thereof comprising administering to the subject a therapeutically effective amount of Compound A and lapatinib, or pharmaceutically acceptable salts thereof.

In another embodiment is a method for treating breast cancer in a subject in need thereof comprising administering to the subject a therapeutically effective amount of Compound B and lapatinib, or pharmaceutically acceptable salts thereof.

In another embodiment is a method for treating breast cancer in a subject in need thereof comprising administering to the subject a therapeutically effective amount of Compound C and lapatinib, or pharmaceutically acceptable salts thereof. This embodiment exhibits synergy (also called potentiation in the Examples) such that sub-therapeutic amounts of Compound C may be used in the method.

In another embodiment is a method for treating breast cancer in a subject in need thereof comprising administering to the subject a therapeutically effective amount of Compound D and lapatinib, or pharmaceutically acceptable salts thereof. This embodiment exhibits synergy (also called potentiation in the Examples) such that sub-therapeutic amounts of Compound D may be used in the method.

In another embodiment is a method for treating breast cancer in a subject in need thereof comprising administering to the subject a therapeutically effective amount of Compound A and a PI3K inhibitor selected from the group consisting of IPI-145, GDC-0941, and CAL-101, or pharmaceutically acceptable salts thereof.

In another embodiment is a method for treating breast cancer in a subject in need thereof comprising administering to the subject a therapeutically effective amount of Compound B and a PI3K inhibitor selected from the group consisting of IPI-145, GDC-0941, and CAL-101, or pharmaceutically acceptable salts thereof.

In another embodiment is a method for treating breast cancer in a subject in need thereof comprising administering to the subject a therapeutically effective amount of Compound C and a PI3K inhibitor selected from the group consisting of IPI-145, GDC-0941, and CAL-101, or pharmaceutically acceptable salts thereof. These embodiments exhibit synergy (also called potentiation in the Examples) such that sub-therapeutic amounts of Compound C may be used in the methods.

In another embodiment is a method for treating breast cancer in a subject in need thereof comprising administering to the subject a therapeutically effective amount of Compound D and a PI3K inhibitor selected from the group consisting of IPI-145, GDC-0941, and CAL-101, or pharmaceutically acceptable salts thereof. These embodiments exhibit synergy (also called potentiation in the Examples) such that sub-therapeutic amounts of Compound D may be used in the methods.

The invention also relates to methods for inhibiting migration and/or invasion of breast cancer cells. In particular, the invention relates to methods for inhibiting migration and/or invasion of breast cancer cells in a subject in need thereof. Specifically, the invention relates to methods for inhibiting migration and/or invasion of breast cancer cells in a subject in need thereof comprising administering to the subject a therapeutically effective amount of an HDAC inhibitor of Formula I or II.

Kits

In other embodiments, kits are provided. Kits according to the invention include package(s) comprising compounds or compositions of the invention. In some embodiments, kits comprise a HDAC inhibitor, or a pharmaceutically acceptable salt thereof, and either a Her2 inhibitor or PI3K inhibitor, or a pharmaceutically acceptable salt thereof.

The phrase "package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering compounds or compositions of the invention to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Definitions of the variables in the structures in the schemes herein are commensurate with those of corresponding positions in the formulae presented herein.

The synthesis of the compounds of Formula I (Compounds A and B) is provided in PCT/US2011/021982, which is incorporated herein by reference in its entirety. The synthesis of compounds of Formula II (Compounds C and D) is provided in PCT/US2011/060791, which is incorporated herein by reference in its entirety.

Example 1

Synthesis of 2-(diphenylamino)-N-(7-(hydroxyamino)-7-oxoheptyl)pyrimidine-5-carboxamide (Compound A)

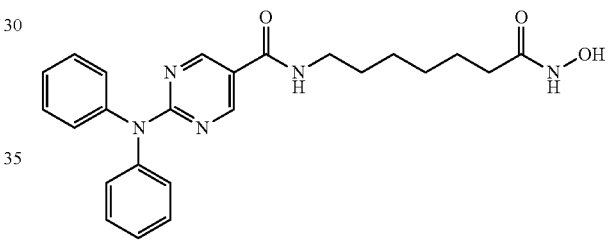

Reaction Scheme

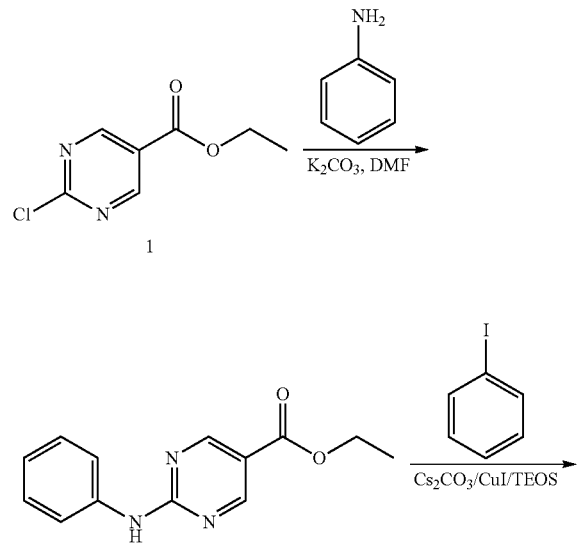

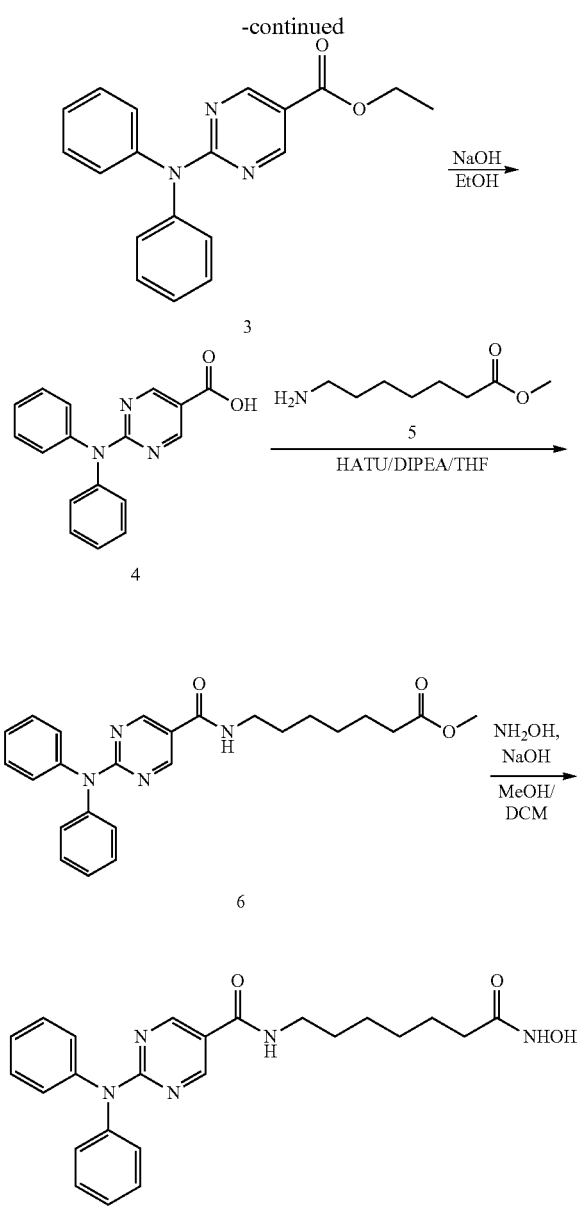

Synthesis of Intermediate 2

A mixture of aniline (3.7 g, 40 mmol), compound 1 (7.5 g, 40 mmol), and $K_2CO_3$ (11 g, 80 mmol) in DMF (100 ml) was degassed and stirred at 120° C. under $N_2$ overnight. The reaction mixture was cooled to r.t. and diluted with EtOAc (200 ml), then washed with saturated brine (200 ml×3). The organic layers were separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3

A mixture of compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4

2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over $Na_2SO_4$. Removal of the solvent gave a brown solid (2.5 g, 92%).

Synthesis of Intermediate 6

A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide (Compound A)

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 2

Synthesis of 2-((2-chlorophenyl)(phenyl)amino)-N-(7-(hydroxyamino)-7-oxoheptyl)pyrimidine-5-carboxamide (Compound B)

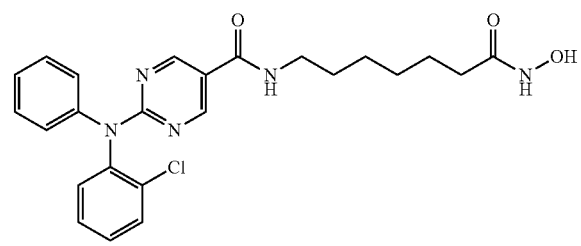 [SMILES: O=C(CCCCCCNC(=O)c1cnc(N(c2ccccc2)c2ccccc2Cl)nc1)NO]

Reaction Scheme:

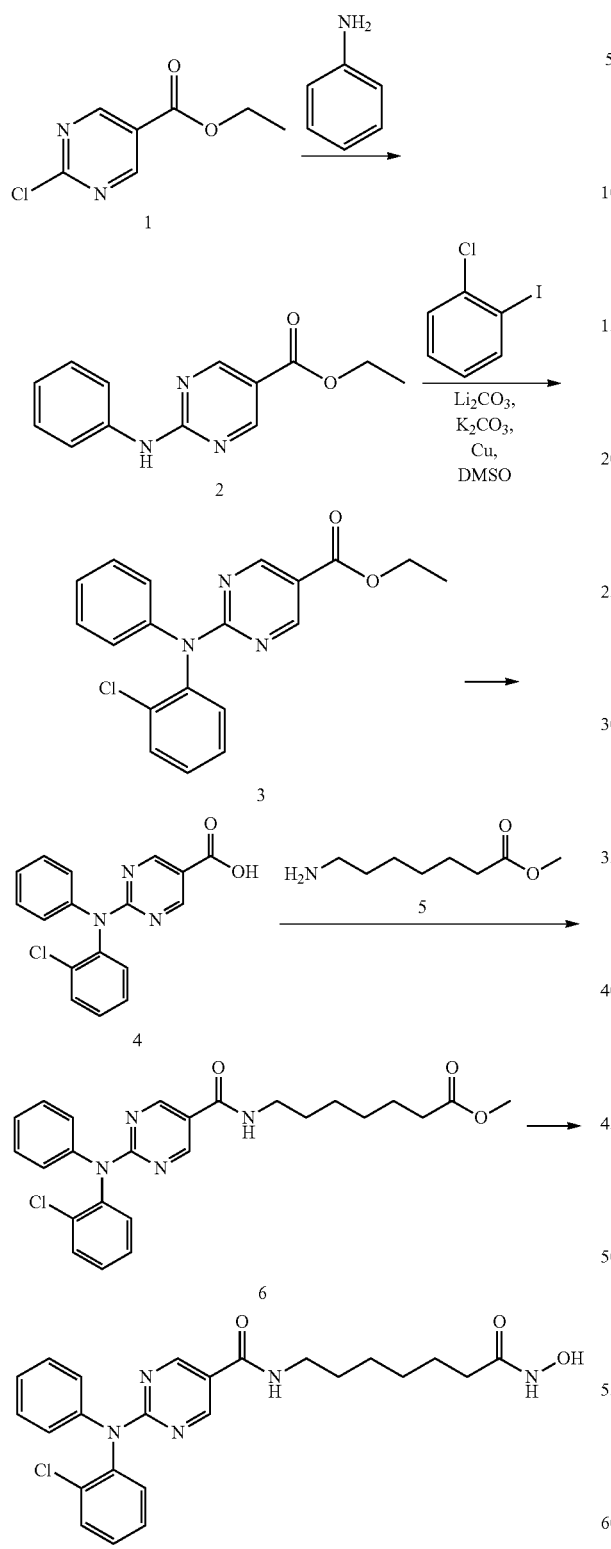

Synthesis of Intermediate 2

See synthesis of intermediate 2 in Example 1.

Synthesis of Intermediate 3

A mixture of compound 2 (69.2 g, 1 equiv.), 1-chloro-2-iodobenzene (135.7 g, 2 equiv.), $Li_2CO_3$ (42.04 g, 2 equiv.), $K_2CO_3$ (39.32 g, 1 equiv.), Cu (1 equiv. 45 µm) in DMSO (690 ml) was degassed and purged with nitrogen. The resulting mixture was stirred at 140° C. Work-up of the reaction gave compound 3 at 93% yield.

Synthesis of Intermediate 4

See synthesis of intermediate 4 in Example 1.

Synthesis of Intermediate 6

See synthesis of intermediate 6 in Example 1.

Synthesis of 2-((2-chlorophenyl)(phenyl)amino)-N-(7-(hydroxyamino)-7-oxoheptyl)pyrimidine-5-carboxamide (Compound B)

See synthesis of Compound A in Example 1.

Example 3

Synthesis of 2-((1-(3-fluorophenyl)cyclohexyl)amino)-N-hydroxypyrimidine-5-carboxamide (Compound C)

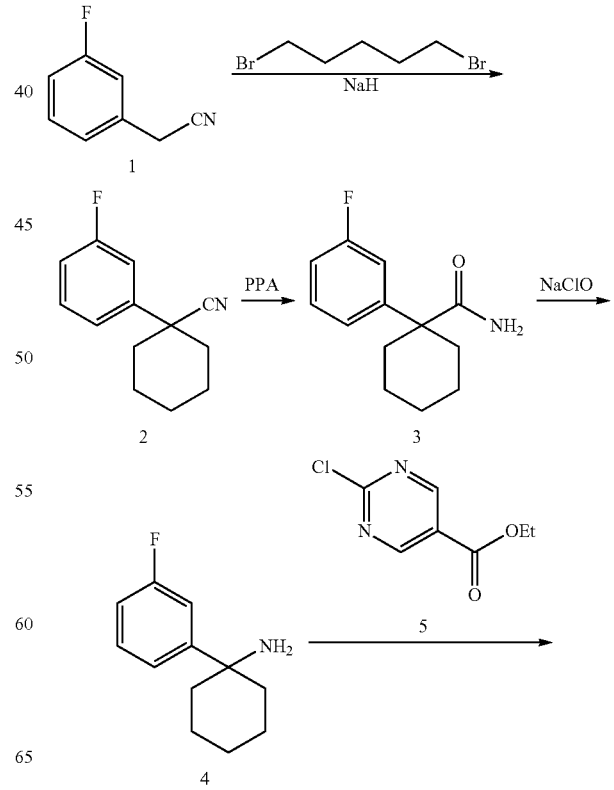

-continued

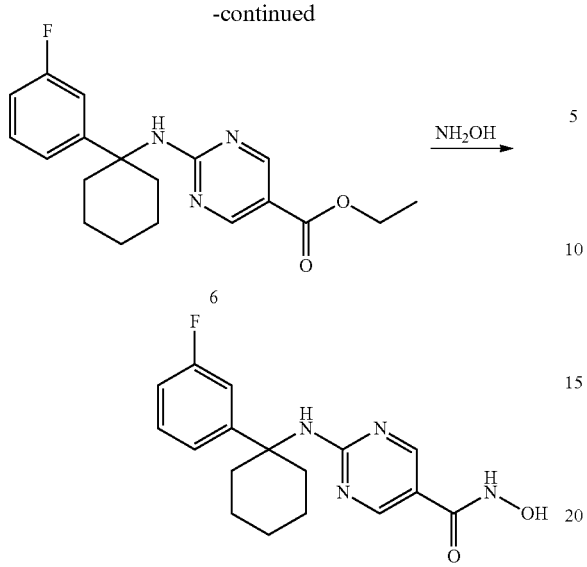

Synthesis of Intermediate 2

To a solution of compound 1 (100 g, 0.74 mol) in dry DMF (1000 ml) was added 1,5-dibromopentane (170 g, 0.74 mol). NaH (65 g, 2.2 eq) was added dropwise while the reaction was cooled in an ice bath. The resulting mixture was vigorously stirred overnight at 50° C. The suspension was carefully quenched with ice water and extracted with ethyl acetate (3×500 ml). The combined organic layers were concentrated to afford the crude product, which was purified by flash column chromatography to give compound 2 as pale solid (100 g, 67%).

Synthesis of Intermediate 3

A solution of compound 2 (100 g, 0.49 mol) in PPA (500 ml) was heated at 110° C. for about 5-6 hours. After completion, the resulting mixture was carefully adjusted to a pH of about 8-9 with sat.NaHCO$_3$ solution. The resulting precipitate was collected and washed with water (1000 ml) to afford compound 3 as white solid (95 g, 87%).

Synthesis of Intermediate 4

To a solution of compound 3 (95 g, 0.43 mol) in n-BuOH (800 ml) was added NaClO (260 ml, 1.4 eq). 3N NaOH (400 ml, 2.8 equiv.) was then added at 0° C. and the reaction was stirred overnight at r.t. The resulting mixture was extracted with EA (2×500 ml), and the combined organic layers washed with brine. The solvent was removed in vacuo to afford the crude product which was further purified by treatment with HCl salt to yield compound 4 as a white powder (72 g, 73%).

Synthesis of Intermediate 6

To a solution of compound 4 (2.29 g 10 mmol) in dioxane (50 ml) was added compound 5 (1.87 g, 1.0 equiv.) and DIPEA (2.58 g, 2.0 equiv.). The mixture was heated overnight at 110-120° C. The resulting mixture was directly purified on silica gel column to afford the coupled product, compound 6, as a white solid (1.37 g, 40%).

Synthesis of 2-((1-(3-fluorophenyl)cyclohexyl)amino)-N-hydroxypyrimidine-5-carboxamide (Compound C)

To a solution of compound 6 (100 mg, 0.29 mmol) in MeOH/DCM (10 ml, 1:1) was added 50% NH$_2$OH in water (2 ml, excess). Sat. NaOH in MeOH (2 ml, excess) was then added at 0° C. and the reaction was stirred for 3-4 hours. After completion, the resulting mixture was concentrated and acidified with 2N HCl to reach a pH of 4-5. The precipitate was collected and washed with water (10 ml) to remove excess NH$_2$OH. Drying the precipitate afforded 2-((1-(3-fluorophenyl)cyclohexyl)amino)-N-hydroxypyrimidine-5-carboxamide as a white powder (70 mg, 73%).

Example 4

Synthesis of N-hydroxy-2-((1-phenylcyclopropyl)amino)pyrimidine-5-carboxamide (Compound D)

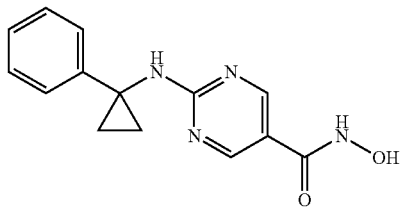 [SMILES: O=C(NO)c1cnc(NC2(c3ccccc3)CC2)nc1]

Reaction Scheme

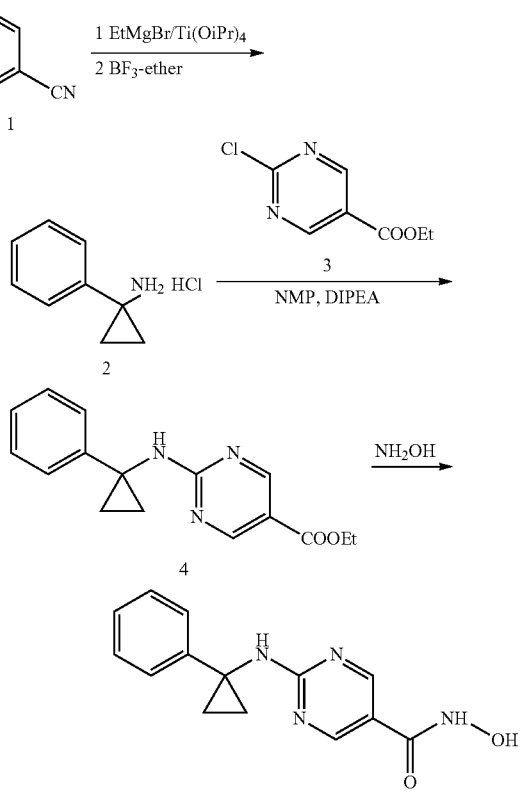

Synthesis of Intermediate 2

A solution of compound 1, benzonitrile, (250 g, 1.0 equiv.), and Ti(OiPr)$_4$ (1330 ml, 1.5 equiv.) in MBTE (3750 ml) was cooled to about −10 to −5° C. under a nitrogen atmosphere. EtMgBr (1610 ml, 3.0M, 2.3 equiv.) was added dropwise over a period of 60 min., during which the inner temperature of the reaction was kept below 5° C. The reaction mixture was allowed to warm to 15-20° C. for 1 hr. BF$_3$-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3 L×2) and EtOAc (3 L×2), and the combined organic layers were dried with anhydrous Na$_2$SO$_4$ and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of compound 2.

Synthesis of Intermediate 4

Compound 2 (620 g, 1.0 equiv) and DIPEA (1080 g, 2.2 equiv. were dissolved in NMP (3100 ml) and stirred for 20 min. Compound 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of compound 4 (solid, 86.8%).

Synthesis of N-hydroxy-2-((1-phenylcyclopropyl)amino)pyrimidine-5-carboxamide (Compound D)

A solution of MeOH (1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hr, and was filtered to remove the solid. Compound 4 (450 g, 1.0 equiv.) was added to the reaction mixture in one portion, and stirred at 10° C. for two hours until compound 4 was consumed. The reaction mixture was adjusted to a pH of about 8.5-9 through addition of HCl (6N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

Example 5

HDAC Enzyme Assays

Compounds for testing were diluted in DMSO to 50 fold the final concentration and a ten point three fold dilution series was made. The compounds were diluted in assay buffer (50 mM HOPES, pH 7.4, 100 mM Kill, 0.001% Tween-20, 0.05% BASE, 20 µM TEC) to 6 fold their final concentration. The HDAC enzymes (purchased from BPS Biosciences) were diluted to 1.5 fold their final concentration in assay buffer. The dipeptide substrate and trypsin at 0.05 µM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 µM (HDAC1), 10 µM (HDAC2), 17 µM (HDAC3) and 14 µM (HDAC6). Five µl of compound and 20 µl of enzyme were added to wells of a black, opaque 384 well plate in duplicate. Enzyme and compound were incubated together at room temperature for 10 min. Five µl of substrate was added to each well, the plate was shaken for 60 seconds and placed into a Victor 2 microliter plate reader. The development of fluorescence was monitored for 60 min. and the linear rate of the reaction was calculated. The IC$_{50}$ was determined using Graph Pad Prism by a four parameter curve fit.

Example 6

Compound A Cytotoxicity and Synergistic Activity with Drug Combinations in Breast Cancer Cells A panel of 16 breast cancer cell lines were treated with either Compound A, doxorubicin, GDC-0941, or lapatinib and the drug combinations for 48 hours, and cell viability was measured by the MTA assay. Synergy between Compound A and the partner compounds were calculated using CalcuSyn. Cell viabilities were used to calculate "Fraction Affected" (Fa) and "Combination Index" (CI) values using the Chou-Talalay method. Any combination with a CI value <0.70 at a Fa value between 0.25 and 0.75 was defined as positive synergy.

The results of the experiment are in the Table below.

| Cells | cmpd A IC$_{50}$ (µM) | + | GDC-0941 IC$_{50}$ (µM) | Synergy | Doxorubicin IC$_{50}$ (µM) | Synergy | Lapatinib IC$_{50}$ (µM) | Synergy |
|---|---|---|---|---|---|---|---|---|
| MDA-MB-453 | 1.25 | | 0.29 | S | 0.22 | — | 0.13 | S |
| SK-BR-3 | 1.94 | | 0.22 | S | 0.12 | S | 0.06 | S |
| BT 474 | 2.32 | | 0.09 | S | 0.19 | S | 0.04 | S |
| ZR-75-1 | 3.57 | | 0.21 | S | 0.13 | S | 2.69 | S |
| MDA-MB-361 | 4.51 | | 3.27 | S | 0.17 | — | 9.31 | — |
| T-47D* | 5.00 | | 0.62 | S | 0.15 | S | 23.33 | S |
| Hs578T | 5.57 | | 1.11 | S | 1.56 | S | 5.77 | S |
| MX-1 | 6.38 | | 0.56 | S | 0.24 | S | 1.01 | S |
| MDA-MB-231 | 7.49 | | 1.69 | S | 0.73 | S | 7.17 | — |
| Bcap-37 | 7.66 | | 2.48 | S | 0.17 | S | 10.91 | S |
| HCC38 | 7.76 | | 7.44 | S | 0.18 | S | 5.05 | S |
| MCF-7 | 8.95 | | 0.43 | S | 0.82 | — | 5.78 | S |
| BT-549 | 8.97 | | 1.66 | S | 0.03 | S | 6.53 | S |
| HCC1937 | 11.25 | | 2.45 | S | 0.24 | S | 5.56 | S |

-continued

| Cells | cmpd A – IC$_{50}$ (μM) | + | GDC-0941 IC$_{50}$ (μM) | Synergy | Doxorubicin IC$_{50}$ (μM) | Synergy | Lapatinib IC$_{50}$ (μM) | Synergy |
|---|---|---|---|---|---|---|---|---|
| MDA-MB-468 | 14.92 | | 2.93 | S | 0.10 | S | 5.60 | S |
| MDA-MB-436 | 25.66 | | 3.27 | S | 0.17 | — | 9.31 | — |

Example 7

PI3K Inhibitor GDC-0941 is Potentiated by HDAC6 Selective Inhibitors

In this example, the potentiation effect of Compound A and Compound C with the PI3K inhibitor GDC-0941 was examined. At non-cytotoxic concentrations of Compound A or Compound C, GDC-0941 becomes more potent (decrease in the IC$_{50}$ value). Both Compound A and Compound C are HDAC6 selective inhibitors with similar low nM potency with 13 fold and 1,500 fold selectivity of HDAC6 over class I HDACs, respectively.

The results of this experiment are shown in FIGS. 1A-D.

Example 8

Potentiation Effect of HDAC6 Inhibitors and the Tested Compounds on Her2$^+$ Breast Cancer Cell Lines To investigate the potentiation effect of the HDAC6 inhibitors, the Her2$^+$ breast cancer cell lines MDA-MB-453 or BT-474 were incubated with combinations of a HDAC6 inhibitor, Compound A or Compound C, and one of the other anti-breast cancer compounds, lapatinib, GDC-0941, CAL-101, or IPI-145. The IC$_{50}$ (Inhibitory Concentration at which 50% of the cells are viable) values of these 4 anti-breast cancer compounds were calculated in the presence of increasing concentrations of a HDAC6 inhibitor. Since Compound A or Compound C alone is not cytotoxic at the tested concentrations to these breast cancer cells, any HDAC6 inhibitor concentration dependent decrease of IC$_{50}$ values suggest a potentiation effect of the HDAC6 inhibitor to the tested compounds.

Example 9

Histone Deacetylase (HDAC) 6 Inhibition Potentiates the Cytotoxicity of Lapatinib and PI3K Inhibitors on Her2$^+$ Breast Cancer Cell Lines In this example, the impact of HDAC6 inhibition has been investigated on Her2$^+$ breast cancer cell growth and cell migration using an HDAC6 inhibitor alone or in combination with either a Her2 inhibitor (lapatinib) or a PI3K inhibitor (GDC-0941, IPI-145, and CAL-101).

Anti-tumor activity of Compound A was investigated using a panel of nearly 100 human tumor cell lines derived from the major cancer types, and Her2$^+$ breast cancer cells were among the most sensitive cells to Compound A. Combinations of Compound A with either the Her2 inhibitor lapatinib or PI3K inhibitor GDC-0941 demonstrated synergistic cytotoxicity against these cancer cells. To illustrate that the effects were due to HDAC6 inhibition, the highly selective HDAC6 inhibitor Compound C was used, which has greater than 1,500 fold of selectivity against HDAC6 over Class I HDACs (HDAC1, 2 and 3). Compound C was able to sensitize Her2$^+$ breast cancer cells MDA-MB-453 and BT-474 to lapatinib and PI3K inhibitors (IPI-145, GDC-0941 and CAL-101). Compound C also blocked cancer cell migration in the presence or absence of epidermal growth factor (EGF). In agreement with the proposed mechanism of HDAC6 mediated Her2$^+$ breast cancer cell death, Compound A treatment correlated with a decrease of Her2 protein, p-EGFR, and p-AKT in the Her2$^+$ breast cancer cell line MDA-MB-453.

By taking advantage of the highly selective HDAC6 inhibitor Compound C, growth and migration suppressive activities by HDAC6 inhibition in Her2$^+$ breast cancer cells were shown.

Example 10

Anti-Migration Effect of HDAC6 Inhibitors on Cancer Cell Lines

Many cultured cancer cells are able to migrate across a membrane and this activity indicates the metastatic potential of the cancer cells. The migration of two cancer cells, A549 and MDA-MB-231, were compared in the presence or absence of a HDAC6 inhibitor. The cancer cells were seeded and grown on a membrane surface, and the cell numbers on the other side of the membrane were counted under a microscope after 12 hours. A decreased number of migrated cells by the HDAC6 inhibitor suggests a migration suppression activity of HDAC6 inhibitor. In the study, an HDAC inhibitor was added to the cells either 2 hours before or when the migration was measured. The effect of HDAC6 inhibitor on Epidermal Growth Factor (EGF) stimulated cancer cell migration using 20 ng/ml of EGF in the assay was investigated.

The protocol for the Migration Assay was as follows. The compounds were prepared in DMSO at 400× stock of the final required concentrations.

| Compound | Final conc. (μM) | Cpds 400* Conc. (μM) |
|---|---|---|
| Tuba A | 5 | 2000 |
| Cmpd C | 5 | 2000 |
| Cmpd A | 0.5 | 200 |
| Gefitinib | 1 | 400 |
| EGF | 20 | 8 |

200 μl of warm basal RPMI1640 medium was added to the interior of the inserts, allowed to rehydrate for 2 hours in a humidified tissue culture incubator at 37° C., 5% CO$_2$ atmosphere. During rehydration, the cells were harvested with trypsin, washed 3 times, and then resuspended with prewarmed basal RPMI1640 medium containing 500,000 cells/ml or 250,000 cells/ml. The compounds were diluted to 20× with basal RPMI1640 medium. 25 μl of 20× compound was added to the 500 μl cell suspension to make the final cell suspension with compound. 100 μl of 20× compound was added to 1,900 μl RPMI1640 medium with 10% FBS to get the final medium, and 500 μl of the final medium was added to the well a new 24-well plate. After rehydration, the medium was removed from the inserts, and then 100 μl final cell suspension was added to the chambers. The chambers were transferred to the wells containing final medium. 100 μl/well of final cell suspension (diluted with final medium to ½ density) was added to a 96-well plate (triplicate). After 8 hours incubation at 37° C., the non-invading cells were removed from the upper surface of the membrane with cotton swabs. Cells on the lower surface of the membrane were fixed with 4% Paraformaldehyde for 15 min at room temperature, and then stained with crystal violet for 30 min. After staining, the inserts were washed in PBS several times to ensure that there is no crystal violet on the membrane, except the cells. The number of migrated cells were counted under a microscope in five fields at 100× magnification. The viable cells were seeded in the 96 well plate with the same treatment as in the migration assay were measured using CTG (Cell Titer Glow).

The results of these experiments are shown in FIGS. 2A-B, 3A-B, and 4A-E.

Example 11

Invasion Effect of HDAC6 Inhibitors on Cancer Cell Lines

The invasion of A549 cancer cells were compared in the presence or absence of a HDAC6 inhibitor. The cancer cells were seeded and grown on a membrane surface, and the cell numbers on the other side of the membrane were counted under a microscope after 12 hours. In addition to migration (Example 10), the cells also had to cross a collagen barrier. A decreased number of migrated cells by the HDAC6 inhibitor suggests an invasion suppression activity of HDAC6 inhibitor. The effect of HDAC6 inhibitor on Epidermal Growth Factor (EGF) stimulated cancer cell migration using 20 ng/ml of EGF in the assay was investigated.

The protocol for the Invasion Assay was as follows. The compounds were prepared in DMSO at 400× stock of the final required concentrations.

| Compound | Final conc. (μM) | Cpds 400* Conc. (μM) |
|---|---|---|
| Tuba A | 5 | 2000 |
| Cmpd C | 5 | 2000 |
| Cmpd A | 0.5 | 200 |
| Gefitinib | 1 | 400 |
| EGF | 20 | 8 |

200 μl of warm basal RPMI1640 medium was added to the interior of the inserts, allowed to rehydrate for 2 hours in a humidified tissue culture incubator at 37° C., 5% $CO_2$ atmosphere. During rehydration, the cells were harvested with trypsin, washed 3 times, and then resuspended with pre-warmed basal RPMI1640 medium containing 500,000 cells/ml or 250,000 cells/ml. The compounds were diluted to 20× with basal RPMI1640 medium. 25 μl of 20× compound was added to the 500 μl cell suspension to make the final cell suspension with compound. 100 μl of 20× compound was added to 1,900 μl RPMI1640 medium with 10% FBS to get the final medium, and 500 μl of the final medium was added to the well a new 24-well plate. After rehydration, the medium was removed from the inserts, and then 100 μl final cell suspension was added to the chambers. The chambers were transferred to the wells containing final medium. 100 μl/well of final cell suspension (diluted with final medium to ½ density) was added to a 96-well plate (triplicate). After 18 hours incubation at 37° C., the non-invading cells were removed from the upper surface of the membrane with cotton swabs. Cells on the lower surface of the membrane were fixed with 4% Paraformaldehyde for 15 min at room temperature, and then stained with crystal violet for 30 min. After staining, the inserts were washed in PBS several times to ensure that there is no crystal violet on the membrane, except the cells. The number of invaded cells were counted under a microscope in five fields at 100× magnification. The viable cells were seeded in the 96 well plate with the same treatment as in the invasion assay were measured using CTG (Cell Titer Glow).

Figure 5:
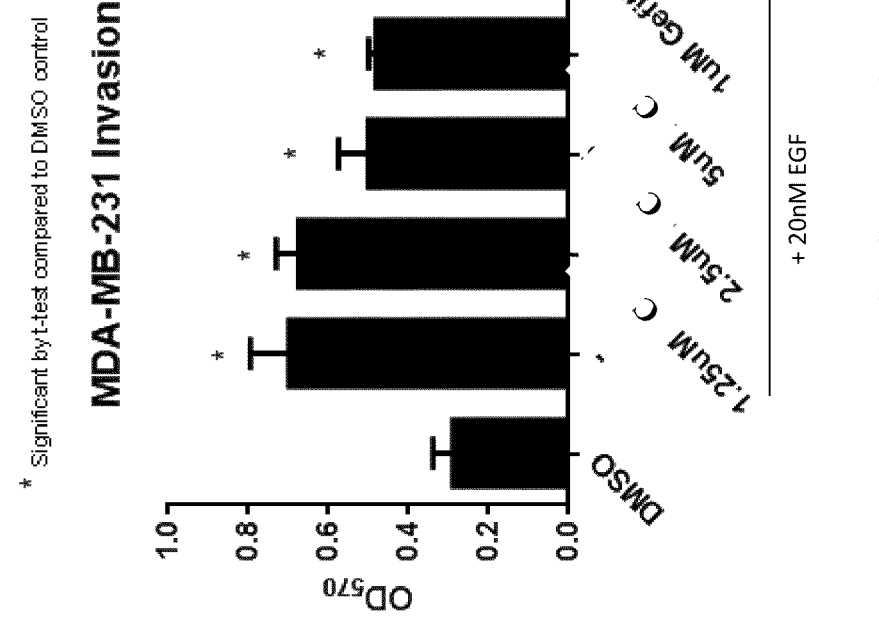
FIGS. 5A-B are a pair of graphs that show the results of invasion assays in A549 cells (lung cancer cells) (FIG. 5A) and MDA-MB-231 cells (breast cancer cells) (FIG. 5B) in which EGF was used to stimulate cancer cell migration. In both assays, Tubastatin A, Compound C, and Compound A were given in concentrations in which the drugs are HDAC6 selective inhibitors. Gefitinib is an EGFR inhibitor.
Figure 5:
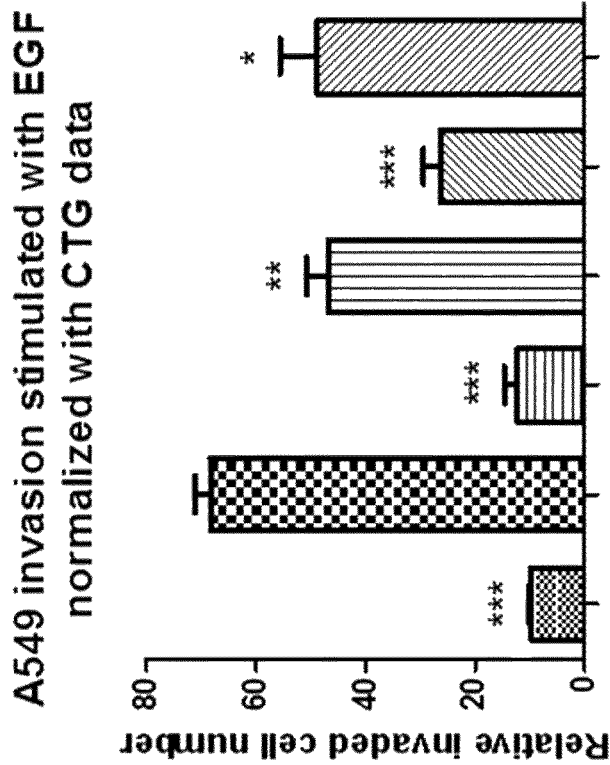

The results of these experiments are shown in FIGS. 5A-B.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A pharmaceutical combination comprising a histone deacetylase (HDAC) inhibitor selected from the group consisting of

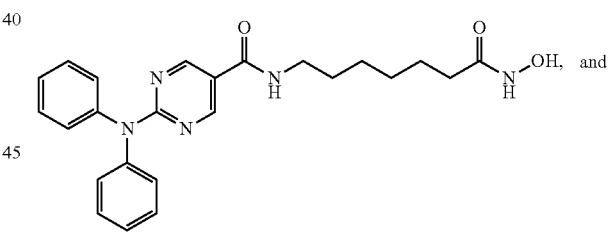

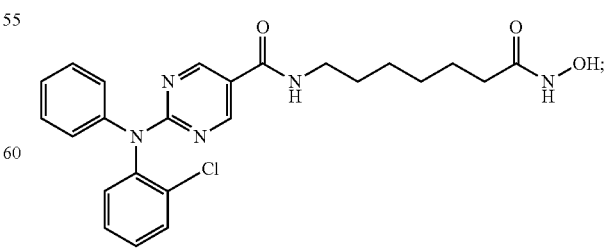

or a pharmaceutically acceptable salt thereof, and a Her2 inhibitor of the formula

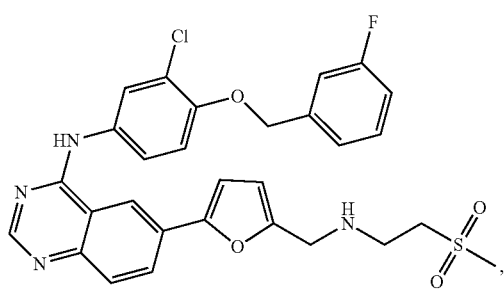 [SMILES: CS(=O)(=O)CCNCc1ccc(-c2ccc3ncnc(Nc4ccc(OCc5cccc(F)c5)c(Cl)c4)c3c2)o1]

or a pharmaceutically acceptable salt thereof.

2. A method of treating breast cancer comprising administering a therapeutically effective amount of the combination of claim 1 to a human patient in need thereof.

3. The pharmaceutical combination of claim 1, wherein the histone deacetylase (HDAC) inhibitor is

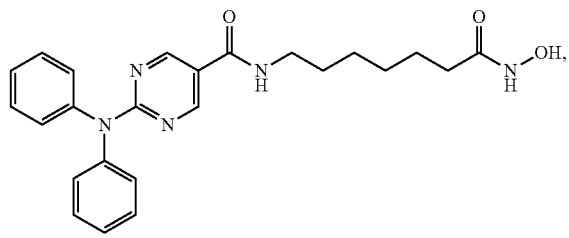 [SMILES: O=C(CCCCCCNC(=O)c1cnc(N(c2ccccc2)c2ccccc2)nc1)NO]

or a pharmaceutically acceptable salt thereof.

4. The pharmaceutical combination of claim 1, wherein the histone deacetylase (HDAC) inhibitor is

or a pharmaceutically acceptable salt thereof.

* * * * *